(12) United States Patent
Boden et al.

(10) Patent No.: US 9,511,071 B2
(45) Date of Patent: Dec. 6, 2016

(54) COMPOUNDS AND COMPOSITIONS FOR OSSIFICATION AND METHODS RELATED THERETO

(75) Inventors: Scott D. Boden, Atlanta, GA (US); Sreedhara Sangadala, Dallas, GA (US)

(73) Assignees: Emory University, Atlanta, GA (US); The United States of America as represented by the Department of Veterans Affairs, Washington, DC (US)

(*) Notice: Subject to any disclaimer, the term of this patent is extended or adjusted under 35 U.S.C. 154(b) by 657 days.

(21) Appl. No.: 13/816,312

(22) PCT Filed: Aug. 18, 2011

(86) PCT No.: PCT/US2011/048252
§ 371 (c)(1),
(2), (4) Date: Feb. 11, 2013

(87) PCT Pub. No.: WO2012/024489
PCT Pub. Date: Feb. 23, 2012

(65) Prior Publication Data
US 2013/0137634 A1    May 30, 2013

Related U.S. Application Data

(60) Provisional application No. 61/374,667, filed on Aug. 18, 2010, provisional application No. 61/479,910, filed on Apr. 28, 2011.

(51) Int. Cl.
| | | |
|---|---|---|
| A61K 31/53 | (2006.01) |
| A61L 27/54 | (2006.01) |
| C07D 251/18 | (2006.01) |
| A61K 38/18 | (2006.01) |

(52) U.S. Cl.
CPC ........... *A61K 31/53* (2013.01); *A61K 38/1875* (2013.01); *A61L 27/54* (2013.01); *C07D 251/18* (2013.01); *A61L 2300/412* (2013.01); *A61L 2430/02* (2013.01)

(58) Field of Classification Search
CPC ..................................................... A61K 31/53
See application file for complete search history.

(56) References Cited

U.S. PATENT DOCUMENTS

| | | |
|---|---|---|
| 2,823,161 A | 2/1958 | Lux |
| 6,489,333 B2 | 12/2002 | Pitts |

(Continued)

FOREIGN PATENT DOCUMENTS

| | | |
|---|---|---|
| WO | 2010085246 | 7/2010 |
| WO | 2011018742 | 2/2011 |

OTHER PUBLICATIONS

Xiang (Synthesis and Bioactivity Study of 4,6-diamino-1,3,5-triazines, National University of Singapore, 2006).*

(Continued)

*Primary Examiner* — Benjamin Packard
(74) *Attorney, Agent, or Firm* — Emory Patent Group

(57) ABSTRACT

The disclosure relates to compounds and compositions for forming bone and methods related thereto. In one embodiment, the disclosure relates to a composition comprising a compound disclosed herein, such as 2,4-diamino-1,3,5-triazine derivatives or salts thereof, for use in bone growth processes. In a typical embodiment, a bone graft composition is implanted in a subject at a site of desired bone growth or enhancement.

18 Claims, 26 Drawing Sheets

(56) References Cited

U.S. PATENT DOCUMENTS

2004/0053061 A1* 3/2004 Yonezawa .............. B32B 15/08
 428/458
2005/0227983 A1* 10/2005 Timmer et al. .............. 514/241
2006/0263355 A1* 11/2006 Quan .................... A61K 31/59
 424/141.1
2008/0033572 A1 2/2008 D'Antonio

OTHER PUBLICATIONS

Scweitzer et al (The FASEB Journal, vol. 4 No. 8 (1990) 2441-2452).*
Hathaway et al. "Inhibition of Human Dibydrofolate Reductase by 4,6-Diamino-1,2-dihydro-2,2-dimethy 1-(substituted-phenyl)-s triazines" J. Med. Chem., 1984; 27: 144-149.
InFUSE™ Bone Graft/LT-CAGE™ Lumbar Tapered Fusion Device, Summary of Safety and Effectiveness Data, 2002.
Kato et al. "A synthetic compound that potentiates bone morphogenetic protein-2-induced transdifferentiation of myoblasts into the osteoblastic phenotype" Mol Cell Biochem., 2011; 349(1-2): 97-106.
Schweitzer et al. "Dihydrofolate reducase as a therapeutic target" The FASEB Journal, 1990; 4: 2441-2451.
Wong et al. "A novel low-molecular-weight compound enhances ectopic bone formation and fracture repair" J Bone Joint Surg, 2013, 95(5):454-461.
Xiang "Synthesis and Bioactivity Study of 4,6-Diamino-1,3,5-Triazines" Thesis submitted for the degree of Doctor of Philosophy Department of Pharmacy, National University of Singapore, 2006.

* cited by examiner

SEQUENCE LISTING

<160> NUMBER OF SEQ ID NOS: 9

<210> SEQ ID NO 1
<211> LENGTH: 396
<212> TYPE: PRT
<213> ORGANISM: Homo sapiens

<400> SEQUENCE: 1

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

```
Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 2
<211> LENGTH: 23
<212> TYPE: PRT
<213> ORGANISM: Artificial Sequence
<220> FEATURE:
<223> OTHER INFORMATION: synthetic peptide fragments of BMP-2

<400> SEQUENCE: 2

Lys Ile Pro Lys Ala Ser Ser Val Pro Thr Glu Leu Ser Ala Ile Ser
1               5                   10                  15

Thr Leu Tyr Leu Asp Asp Asp
            20
```

-continued

```
<210> SEQ ID NO 3
<211> LENGTH: 28
<212> TYPE: PRT
<213> ORGANISM: Artificial Sequence
<220> FEATURE:
<223> OTHER INFORMATION: synthetic peptide fragments of BMP-2

<400> SEQUENCE: 3

Cys Cys Cys Cys Asp Asp Asp Ser Lys Ile Pro Lys Ala Ser Ser Val
1               5                   10                  15

Pro Thr Glu Leu Ser Ala Ile Ser Thr Leu Tyr Leu
            20                  25

<210> SEQ ID NO 4
<211> LENGTH: 33
<212> TYPE: PRT
<213> ORGANISM: Artificial Sequence
<220> FEATURE:
<223> OTHER INFORMATION: synthetic peptide fragments of BMP-2
<220> FEATURE:
<221> NAME/KEY: MISC_FEATURE
<222> LOCATION: (3)..(3)
<223> OTHER INFORMATION: V = O

<400> SEQUENCE: 4

Cys His Val Asn His Cys Cys Cys Gly Gly Gly Ser Lys Ile Pro
1               5                   10                  15

Lys Ala Ser Ser Val Pro Thr Glu Leu Ser Ala Ile Ser Thr Leu Tyr
            20                  25                  30

Leu

<210> SEQ ID NO 5
<211> LENGTH: 431
<212> TYPE: PRT
<213> ORGANISM: Homo sapiens

<400> SEQUENCE: 5

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175
```

```
Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Asn Val Val Arg Ala Cys Gly Cys His
            420                 425                 430

<210> SEQ ID NO 6
<211> LENGTH: 21
<212> TYPE: DNA
<213> ORGANISM: Artificial Sequence
<220> FEATURE:
<223> OTHER INFORMATION: ALP forward Primer

<400> SEQUENCE: 6
tcagggcaat gaggtcacat c                                        21

<210> SEQ ID NO 7
<211> LENGTH: 19
<212> TYPE: DNA
<213> ORGANISM: Artificial Sequence
<220> FEATURE:
<223> OTHER INFORMATION: ALP reverse primer

<400> SEQUENCE: 7
cacaatgccc acggacttc                                           19

<210> SEQ ID NO 8
<211> LENGTH: 20
<212> TYPE: DNA
<213> ORGANISM: Artificial Sequence
<220> FEATURE:
<223> OTHER INFORMATION: Osteocalcin forward primer
```

```
<400> SEQUENCE: 8
cggccctgag tctgacaaag                                            20

<210> SEQ ID NO 9
<211> LENGTH: 20
<212> TYPE: DNA
<213> ORGANISM: Artificial Sequence
<220> FEATURE:
<223> OTHER INFORMATION: Osteocalcin reverse primer

<400> SEQUENCE: 9
ctcgtcacaa gcagggtcaa                                            20
```

COMPOUNDS AND COMPOSITIONS FOR OSSIFICATION AND METHODS RELATED THERETO

This application claims priority to U.S. provisional application No. 61/374,667 filed Aug. 18, 2010 and U.S. provisional application No. 61/479,910 filed Apr. 28, 2011, both hereby incorporated by reference.

ACKNOWLEDGEMENTS

This invention was made with government support under Grant No. AR053093 awarded by the National Institutes of Health. The government has certain rights in the invention.

FIELD

The disclosure relates to compounds and compositions for forming bone and methods related thereto. In one embodiment, the disclosure relates to a composition comprising a compound disclosed herein, such as 2,4-diamino-1,3,5-triazine derivatives or salts thereof, for use in bone growth processes. In a typical embodiment, a bone graft composition is implanted in a subject at a site of desired bone growth or enhancement.

BACKGROUND

Bone grafting is typically performed for spinal fusions, after cancerous bone removal, and in certain operations, e.g., plastic surgery. The iliac crest is often used as a donor site for autologous grafts. Complications collecting bone from the iliac crest include pain, nerve damage, hematoma and wound complications, avulsion of the anterior superior iliac spine (ASIS), hematoma, herniation of the abdominal cavity contents, and cosmetic deformity. Thus, it is desirable to develop materials and methods of forming bone that do not require harvesting bone from remote sites of the patient.

Synthetic bone grafts typically include a matrix that holds minerals and other salts. Natural bone has an intracellular matrix mainly composed of type I collagen, and some synthetic bone grafts include a collagen matrix. Synthetic bone grafts typically contain bone growths factors such as bone morphogenetic proteins (BMPs) because of their ability to induce ossification in the matrix material. Recombinant human BMP-2 has been approved by the FDA in synthetic bone grafts such as INFUSE™. INFUSE™ is approved for open tibial shaft fractures, lumbar interbody fusion, and sinus and alveolar ridge augmentations. However, the high cost and need for high concentrations of BMP-2 for treatment creates a barrier for routine clinical use. Thus, there is a need to identify additional compositions that can substitute or complement the use of BMPs in treating bone-related conditions.

Cellular response to BMPs depends on a complex set of interactions typically involving intracellular signaling proteins known as Smads. The baseline levels of Smads are in part affected by their ability to interact with Smurf1, a key regulator of the degradation of BMP-2 signaling molecules, Smad1 and Smad5. Smurf1 interacts with Smad1/5 and targets them for degradation, thus, leading to reduced BMP signaling.

SUMMARY

The disclosure relates to compounds and compositions for ossification and methods related thereto. In certain embodiments, it is an object of the disclosure to provide certain compounds, compositions, and methods of using compounds to improve bone grafting or to induce bone formation in a subject. In typical embodiment, the bone graft composition comprises a compound that modulates Smurf1 interaction with its natural target proteins in cells. In specific embodiments, the disclosure relates to compounds disclosed herein, such as 2,4-diamino-1,3,5-triazine derivatives or salts thereof, and compositions including such compounds, as well as their methods of use. The 2,4-diamino-1,3,5-triazine derivatives can be, for example, 2,4-diamino-6-vinyl-1,3,5-triazine (Compound 12) or compound 12X: 1-(4-chlorophenyl)-4,6-diamino-1,2-dihydro-2,2-dimethyl-1,3,5-triazine. In certain embodiments, the composition further comprises a bone morphogenetic protein and/or another growth factor. Typically, the bone morphogenetic protein is BMP-2 or BMP-7. In certain embodiments, the graft composition comprises calcium phosphates and/or bone granules, hydroxyapatite and/or beta-tricalcium phosphate, alpha-tricalcium phosphate, polysaccharides or combinations thereof. Crushed bone granules, typically obtained from the subject, are optionally added to the graft composition.

In some embodiments, the 2,4-diamino-1,3,5-triazine derivatives have formula I:

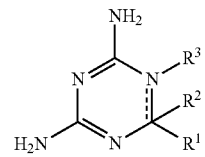

Formula I or a salt thereof, wherein if ---- is a single bond then $R^3$ is carbocyclyl, aryl, or heterocyclyl wherein $R^3$ is optionally substituted with one or more the same or different $R^4$, or $R^3$ is alkyl, phenyl, benzyl, carbocyclyl, aryl, or heterocyclyl wherein $R^3$ is optionally substituted with one or more the same or different $R^4$, $R^2$ is hydrogen or alkyl, such as methyl, and $R^1$ is hydrogen or alkyl; or if ---- is a double bond then $R^1$ is alkyl, alkenyl, carbocyclyl, aryl, or heterocyclyl wherein $R^1$ is optionally substituted with one or more the same or different $R^4$; and $R^2$ and $R^3$ are absent;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, ---- is a single bond, $R^3$ is alkyl, phenyl, benzyl, carbocyclyl, aryl, or heterocyclyl wherein $R^3$ is optionally substituted with one or more the same or different $R^4$, and $R^1$ and $R^2$ are each the same or different alkyl, such as methyl. In certain embodiments, $R^4$ is halogen, alkyl, alkoxy, or hydroxy.

In some embodiments, the disclosure relates to a bone graft compositions comprising a compound disclosed herein, such as a 2,4-diamino-1,3,5-triazine derivative, or a salt thereof, and a graft matrix. Typically, the matrix comprises a collagen sponge and/or a compression resistant type I collagen and calcium phosphates. In other embodiments, the matrix is a hydrogel.

In some embodiments, the disclosure relates to kits comprising a graft composition, a compound disclosed herein, such as a 2,4-diamino-1,3,5-triazine derivative, or a salt thereof, and a graft matrix. In certain embodiments, the kits further comprise a bone morphogenetic protein and/or another growth factor. In certain embodiments, the kits further comprise a transfer device, such as a syringe or pipette.

In some embodiments, the disclosure relates to methods of generating BMP-mediated osteoblasts comprising administering an effective amount of compound(s) disclosed herein to cells capable of osteoblastic differentiation, such as mesenchymal stem cells and pre-osteoblastic cells.

In some embodiments, the disclosure relates to methods of forming bone or cartilage, comprising implanting a graft composition comprising a compound disclosed herein, such as a 2,4-diamino-1,3,5-triazine derivative, or a salt thereof, in a subject under conditions such that bone or cartilage forms in the graft. Typically, the subject has a void in the bony structure wherein the graft composition is implanted in the void. In certain embodiments, the void is in a bone selected from an extremity, maxilla, mandible, pelvis, spine and/or cranium. In certain embodiments, the void is a result of surgical removal of bone. In certain embodiments, the void is between bone and an implanted medical device. In another embodiment, the method further comprises the step of securing movement of bone structure with a fixation system, and removing the system after bone forms in the implanted graft.

In certain embodiments, the disclosure relates to uses of 2,4-diamino-1,3,5-triazine derivatives or salts thereof for cartilage regeneration e.g., between intervertebral disc and articular, jaw, elbow, knee, ankle, wrist, and hip joints. Methods contemplate oral administration, intravenous administration, or direct injection at the desired site(s) of the subject.

In some embodiments, the disclosure relates to methods of performing spinal fusion comprising implanting a bone graft composition comprising a compound disclosed herein, such as a 2,4-diamino-1,3,5-triazine derivative, or a salt thereof, configured to grow bone between two vertebrae of a subject. In certain embodiments, the composition further comprises a bone morphogenetic protein and/or another growth factor. In a typical embodiment, the subject is diagnosed with degenerative disc disease or has symptoms of back pain.

In some embodiments, the disclosure relates to methods of inserting a prosthetic device or anchor, comprising exposing a bone; and implanting a graft composition comprising a compound disclosed herein, such as a 2,4-diamino-1,3,5-triazine derivative, or a salt thereof, in contact with the bone. In certain embodiments, one implants the prosthetic device or anchor in the graft composition. In certain embodiments, the composition further comprises a bone morphogenetic protein and/or another growth factor.

In some embodiments, the disclosure relates to pharmaceutical compositions comprising compounds disclosed herein, such as 2,4-diamino-1,3,5-triazine derivatives, or a pharmaceutically acceptable salts thereof. In certain embodiments, the composition further comprises a bone morphogenetic protein and/or another growth factor. In certain embodiments, the pharmaceutical composition is formulated to release over a 12 hour, 1 day, 3 day, 5 day, 7 day, two week, or one month period.

In certain embodiments, the disclosure relates to methods of preventing or treating a bone fracture, comprising administering a pharmaceutical composition comprising a compound disclosed herein, such as a 2,4-diamino-1,3,5-triazine derivative, or a pharmaceutically acceptable salt thereof, to a subject at risk for, exhibiting symptoms of, or diagnosed with a bone fracture. In certain embodiments, the composition further comprises a bone morphogenetic protein and/or another growth factor. In certain embodiments, the administration is localized. In certain embodiments, administration is achieved through oral delivery, intravenous delivery, parenteral delivery, intradermal delivery, percutaneous delivery, or subcutaneous delivery. In some embodiments, the method further comprises the step of exposing the bone fracture to pulsed electromagnetic fields. In further embodiments, the subject is diagnosed with a long bone shaft fracture such as a tibia or femur fracture corrected with intramedullary nail fixation.

In some embodiments, the disclosure relates to methods of preventing or treating a bone degenerative disease, comprising administering a pharmaceutical composition comprising a compound disclosed herein, such as a 2,4-diamino-1,3,5-triazine derivative, or a pharmaceutically acceptable salt thereof, to a subject at risk for, exhibiting symptoms of, or diagnosed with a bone degenerative disease. In certain embodiments, the composition further comprises a bone morphogenetic protein and/or another growth factor. In certain embodiments, the administration is systemic, or administration is achieved through oral delivery, intravenous delivery, parenteral delivery, intradermal delivery, percutaneous delivery, or subcutaneous delivery. In some embodiments, the disease is osteoporosis, osteitis deformans, bone metastasis, multiple myeloma, primary hyperparathyroidism, or osteogenesis imperfecta.

In some embodiments, the disclosure relates to methods for decreasing the time required to form new bone in the presence of a bone morphogenetic protein, comprising co-administering at least one compound disclosed herein, such as a 2,4-diamino-1,3,5-triazine derivative, or a salt thereof.

In some embodiments, the disclosure relates to a process for engineering bone tissue comprising combining a compound disclosed herein, such as a 2,4-diamino-1,3,5-triazine derivative, or a salt thereof, and optionally a bone morphogenetic protein, with a cell selected from the group consisting of osteogenic cells, pluripotent stem cells, mesenchymal cells, and embryonic stem cells.

In some embodiments, the disclosure relates to compositions and methods disclosed herein wherein the 2,4-diamino-1,3,5-triazine derivative is a 1-(phenyl)-5-isopropyl-biguanide or a salt thereof optionally substituted with one or more substituents. In certain embodiments, the 2,4-diamino-1,3,5-triazine derivative has formula II:

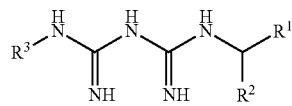

Formula II or a salt thereof wherein $R^1$ is hydrogen or alkyl; $R^2$ is hydrogen or alkyl, such as methyl, and $R^3$ is alkyl, phenyl, benzyl, carbocyclyl, aryl, or heterocyclyl optionally substituted with one or more the same or different $R^4$;

R⁴ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R⁵; and R⁵ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, R³ is phenyl substituted with one or more halogens.

In certain embodiments, the 1-(phenyl)-5-isopropyl-biguanide derivative is proguanil, 1-(4-chlorophenyl)-5-isopropyl-biguanide hydrochloride or salt thereof. These compounds can be used in promotion of bone growth and for the treatment of osteoporosis and other bone growth related diseases and disorders. In some embodiments, the disclosure relates to compositions and methods disclosed herein wherein the 2,4-diamino-1,3,5-triazine derivative is an aromatic triazine or an aromatic 1,3,5-triazine such as:

2,4-diamino-6-phenyl-1,3,5-triazine,
2-chloro-4,6-diamino-1,3,5-triazine,
6-methyl-1,3,5-triazine-2,4-diamine,
2,4-diamino-1,3,5-triazine,
2,4-diamino-6-(2,3-xylyl)-1,3,5-triazine,
2,4-diamino-6-(m-tolyl)-1,3,5-triazine,
2,4-diamino-6-isobutyryl-1,3,5-triazine,
2,4-diamino-6-phenylacetyl-1,3,5-triazine,
4,6-diamino-2-hydroxy-1,3,5-triazine,
2-chloro-4,6-bis(ethylamino)-1,3,5-triazine,
4,6-dimethyl-1,3,5-triazin-2-amine,
6-methyl-1,3,5-triazine-2,4-diamine,
2,4-diamino-6-(2-fluorophenyl)-1,3,5-triazine,
2,4,diamino-6-(3,5-difluorophenyl)-1,3,5-triazine,
2,4-diamino-6-(3-fluorophenyl)-1,3,5-triazine,
2,4-diamino-6-(4-bromophenyl)-1,3,5-triazine,
6-(4-chlorophenyl)-1,3,5-triazine-2,4-diamine,
2,4-diamino-6-(4-methoxphenyl)-1,3,5-triazine,
2,4-diamino-6-(4-methylphenyl)-1,3,5-triazine,
2,4-diamino-6-(3-nitrophenyl)-1,3,5-triazine,
4,6-diamino-gamma-oxo-1,3,5-triazine-2-butyric acid,
4,6-diamino-gamma-oxo-1,3,5-triazine-2-butyronitrile,
2,4-diamino-6-vinyl-1,3,5-triazine,
6-propyl-1,3,5-triazine-2,4-diamine,
6-isobutyl-1,3,5-triazine-2,4-diamine, or salts thereof.

In some embodiments, the disclosure relates to compositions and methods disclosed herein wherein the 2,4-diamino-1,3,5-triazine derivative is a non-aromatic triazine or a non-aromatic 1,3,5-triazine such as:

1-(4-chlorophenyl)-4,6-diamino-1,2-dihydro-2,2-dimethyl-1,3,5-triazine,1-isopropyl-4,6-diamino-1,2-dihydro-2,2-dimethyl-1,3,5-triazine,
1-isobutyl-4,6-diamino-1,2-dihydro-2,2-dimethyl-1,3,5-triazine,
1-(4-chlorophenyl)-4,6-diamino-1,2-dihydro-2,2-dimethyl-1,3,5-triazine,
6,6-dimethyl-1-(2-methylbutyl)-1,6-dihydro-1,3,5-triazine-2,4-diamine,
1-(cyclopropylmethyl)-4,6-diamino-1,2-dihydro-2,2-dimethyl-1,3,5-triazine,
1-(2-methoxyethyl)-4,6-diamino-1,2-dihydro-2,2-dimethyl-1,3,5-triazine,
1-benzyl-4,6-diamino-1,2-dihydro-2,2-dimethyl-1,3,5-triazine,
1-(4-methoxybenzyl)-4,6-diamino-1,2-dihydro-2,2-dimethyl-1,3,5-triazine,
1-(3-methoxybenzyl)-4,6-diamino-1,2-dihydro-2,2-dimethyl-1,3,5-triazine,
1-(4-bromo-2-fluorophenyl)-4,6-diamino-1,2-dihydro-2,2-dimethyl-1,3,5-triazine,
1-(2-bromo-4-methylphenyl)-4,6-diamino-1,2-dihydro-2,2-dimethyl-1,3,5-triazine,
6,6-dimethyl-1-(4-methyl-3-nitrophenyl)-1,6-dihydro-1,3,5-triazine-2,4-diamine,
1-(2,4-difluorophenyl)-4,6-diamino-1,2-dihydro-2,2-dimethyl-1,3,5-triazine,
1-(2-fluoro-4-iodophenyl)-4,6-diamino-1,2-dihydro-2,2-dimethyl-1,3,5-triazine,
1-(4-bromo-2-methylphenyl)-4,6-diamino-1,2-dihydro-2,2-dimethyl-1,3,5-triazine,
1-(3-chlorophenyl)-4,6-diamino-1,2-dihydro-2,2-dimethyl-1,3,5-triazine,
1-(2-fluorophenyl)-4,6-diamino-1,2-dihydro-2,2-dimethyl-1,3,5-triazine,
1-(3-chloro-4-methoxyphenyl)-4,6-diamino-1,2-dihydro-2,2-dimethyl-1,3,5-triazine,
1-(4-chloro-2,5-dimethoxyphenyl)-4,6-diamino-1,2-dihydro-2,2-dimethyl-1,3,5-triazine,
1-(4-chloro-2-fluorophenyl)-4,6-diamino-1,2-dihydro-2,2-dimethyl-1,3,5-triazine,
1-(4-chloro-2-methylphenyl)-4,6-diamino-1,2-dihydro-2,2-dimethyl-1,3,5-triazine,
5-chloro-2-(4,6-diamino-2,2-dimethyl-1,3,5-triazin-1(2H)-yl)benzoic acid,
5-chloro-2-(4,6-diamino-2,2-dimethyl-1,3,5-triazin-1(2H)-yl)-3-methylbenzonitrile,
1-(4-chloro-2-methoxyphenyl)-4,6-diamino-1,2-dihydro-2,2-dimethyl-1,3,5-triazine,
1-(3-chloro-4-methylphenyl)-4,6-diamino-1,2-dihydro-2,2-dimethyl-1,3,5-triazine,
1-(5-chloro-2,4-dimethoxyphenyl)-4,6-diamino-1,2-dihydro-2,2-dimethyl-1,3,5-triazine,
1-(3-chloro-4-ethylphenyl)-4,6-diamino-1,2-dihydro-2,2-dimethyl-1,3,5-triazine,
1-(3-chloro-5-fluorophenyl)-4,6-diamino-1,2-dihydro-2,2-dimethyl-1,3,5-triazine,
2-chloro-4-(4,6-diamino-2,2-dimethyl-1,3,5-triazin-1(2H)-yl)phenol,
1-(5-chloro-2-methoxyphenyl)-4,6-diamino-1,2-dihydro-2,2-dimethyl-1,3,5-triazine,
3-chloro-4-(4,6-diamino-2,2-dimethyl-1,3,5-triazin-1(2H)-yl)-5-methylbenzonitrile,
1-(3-chloro-5-methoxyphenyl)-4,6-diamino-1,2-dihydro-2,2-dimethyl-1,3,5-triazine,
1-(2-chloro-5-methoxyphenyl)-4,6-diamino-1,2-dihydro-2,2-dimethyl-1,3,5-triazine,
1-(2-chloro-4-methylphenyl)-4,6-diamino-1,2-dihydro-2,2-dimethyl-1,3,5-triazine,
1-(5-chloro-2-methylphenyl)-4,6-diamino-1,2-dihydro-2,2-dimethyl-1,3,5-triazine,
1-(5-chloro-2-ethylphenyl)-4,6-diamino-1,2-dihydro-2,2-dimethyl-1,3,5-triazine,
1-(2-chloro-4-methoxyphenyl)-4,6-diamino-1,2-dihydro-2,2-dimethyl-1,3,5-triazine, methyl 3-chloro-4-(4,6-diamino-2,2-dimethyl-1,3,5-triazin-1(2H)-yl)benzoate,
3-chloro-4-(4,6-diamino-2,2-dimethyl-1,3,5-triazin-1(2H)-yl)phenol,
1-(2-chloro-6-methylphenyl)-4,6-diamino-1,2-dihydro-2,2-dimethyl-1,3,5-triazine,
1-(4-fluoro-2-methylphenyl)-4,6-diamino-1,2-dihydro-2,2-dimethyl-1,3,5-triazine,
3-chloro-4-(4,6-diamino-2,2-dimethyl-1,3,5-triazin-1(2H)-yl)benzonitrile,
1-(2-chloro-6-fluorophenyl)-4,6-diamino-1,2-dihydro-2,2-dimethyl-1,3,5-triazine,
1-(3-chloro-4-fluorophenyl)-4,6-diamino-1,2-dihydro-2,2-dimethyl-1,3,5-triazine,
(5-chloro-2-(4,6-diamino-2,2-dimethyl-1,3,5-triazin-1(2H)-yl)phenyl)methanol,
1-(4-chloro-3-methoxyphenyl)-4,6-diamino-1,2-dihydro-2,2-dimethyl-1,3,5-triazine,
1-(3-chloro-4-methoxyphenyl)-4,6-diamino-1,2-dihydro-2,2-dimethyl-1,3,5-triazine,
1-(4-bromo-2-fluorobenzyl)-4,6-diamino-1,2-dihydro-2,2-dimethyl-1,3,5-triazine,
1-(2,6-difluorobenzyl)-4,6-diamino-1,2-dihydro-2,2-dimethyl-1,3,5-triazine,
1-(3-bromo-4-fluorobenzyl)-4,6-diamino-1,2-dihydro-2,2-dimethyl-1,3,5-triazine,
4-[4,6-d]amino-2,2-dimethyl-1,3,5-triazin-1(2H)-yl)methyl)-2-methoxyphenol,
1-(3-chloro-4-fluorobenzyl)-4,6-diamino-1,2-dihydro-2,2-dimethyl-1,3,5-triazine,
1-(2,4-dimethoxybenzyl)-4,6-diamino-1,2-dihydro-2,2-dimethyl-1,3,5-triazine,
1-(5-bromo-2-fluorobenzyl)-4,6-diamino-1,2-dihydro-2,2-dimethyl-1,3,5-triazine,
1-(3,5-difluorobenzyl)-4,6-diamino-1,2-dihydro-2,2-dimethyl-1,3,5-triazine,
1-(3,4-dimethoxybenzyl)-4,6-diamino-1,2-dihydro-2,2-dimethyl-1,3,5-triazine,
6,6-dimethyl-1-(3-(trifluoromethyl)benzyl)-1,6-dihydro-1,3,5-triazine-2,4-diamine,
1-(3-fluorobenzyl)-4,6-diamino-1,2-dihydro-2,2-dimethyl-1,3,5-triazine,
1-(4-fluorobenzyl)-4,6-diamino-1,2-dihydro-2,2-dimethyl-1,3,5-triazine,
1-(5-bromo-2-fluorobenzyl)-4,6-diamino-1,2-dihydro-2,2-dimethyl-1,3,5-triazine, and
6,6-dimethyl-1-(3-nitrobenzyl)-1,6-dihydro-1,3,5-triazine-2,4-diamine or salts thereof.

In certain embodiments, the 2,4-diamino-1,3,5-triazine derivative is a compound selected from the group consisting of:
1-benzyl-4,6-diamino-1,2-dihydro-2,2-dimethyl-1,3,5-triazine;
1-(4-methoxybenzyl)-4,6-diamino-1,2-dihydro-2,2-dimethyl-1,3,5-triazine;
1-(3-methoxybenzyl)-4,6-diamino-1,2-dihydro-2,2-dimethyl-1,3,5-triazine;
1-(4-chlorophenyl)-4,6-diamino-1,2-dihydro-2,2-dimethyl-1,3,5-triazine;
1-(3-chlorophenyl)-4,6-diamino-1,2-dihydro-2,2-dimethyl-1,3,5-triazine;
1-(3-chloro-4-methoxyphenyl)-4,6-diamino-1,2-dihydro-2,2-dimethyl-1,3,5-triazine;
1-(3-chloro-4-methylphenyl)-4,6-diamino-1,2-dihydro-2,2-dimethyl-1,3,5-triazine;
1-(4-bromo-2-fluorophenyl)-4,6-diamino-1,2-dihydro-2,2-dimethyl-1,3,5-triazine;
1-(2-bromo-4-methylphenyl)-4,6-diamino-1,2-dihydro-2,2-dimethyl-1,3,5-triazine;
6,6-dimethyl-1-(4-methyl-3-nitrophenyl)-1,6-dihydro-1,3,5-triazine-2,4-diamine;
1-(3-chloro-4-fluorophenyl)-4,6-diamino-1,2-dihydro-2,2-dimethyl-1,3,5-triazine;
1-(3-chloro-5-fluorophenyl)-4,6-diamino-1,2-dihydro-2,2-dimethyl-1,3,5-triazine;
2-chloro-4-(4,6-diamino-2,2-dimethyl-1,3,5-triazin-1(2H)-yl)phenol;
1-(2-chloro-5-methoxyphenyl)-4,6-diamino-1,2-dihydro-2,2-dimethyl-1,3,5-triazine; and
1-(2-chloro-4-methylphenyl)-4,6-diamino-1,2-dihydro-2,2-dimethyl-1,3,5-triazine or salts thereof.

In certain embodiments, the disclosure relates to any of the 2,4-diamino-1,3,5-triazine derivatives disclosed herein, substituted with one or more substituents.

In certain embodiments, the disclosure relates to methods of making compounds disclosed herein by mixing an amine and guanidine, guanidine salt, or imine formed from a ketone or aldehyde to guanidine under conditions such that compounds disclosed herein are formed.

In certain embodiments, the disclosure relates to using 2,4-diamino-1,3,5-triazine derivatives disclosed herein in the production of a medicament for the treatment or prevention of a bone disease or other applications disclosed herein.

In certain embodiments, the disclosure relates to a bone graft composition comprising a bone growth-inducing amount of a 2,4-diamino-1,3,5-triazine derivative or salt thereof, and a pharmaceutically acceptable carrier.

In certain embodiments, the 2,4-diamino-1,3,5-triazine derivative has formula I or salts thereof, wherein
(A) if ---- is a single bond, then $R^3$ is alkyl, phenyl, benzyl, carbocyclyl, aryl, or heterocyclyl optionally substituted with one or more the same or different $R^4$, $R^2$ is hydrogen or alkyl, and $R^1$ is hydrogen or alkyl; or
(B) if ---- is a double bond, then $R^1$ is alkyl, alkenyl, carbocyclyl, aryl, or heterocyclyl optionally substituted with one or more the same or different $R^4$, and $R^2$ and $R^3$ are absent;
$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$ groups; and
$R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, ---- is a single bond; $R^3$ is alkyl, phenyl, benzyl, carbocyclyl, aryl, or heterocyclyl, optionally substituted with one or more of the same or different $R^4$ groups; $R^2$ is hydrogen or alkyl; and $R^1$ is hydrogen or alkyl.

In certain embodiments, the 2,4-diamino-1,3,5-triazine derivative is a 1-(phenyl)-5-isopropyl-biguanide or salt thereof optionally substituted with one or more substituents.

In certain embodiments, the bone graft composition further comprises a growth factor.

In certain embodiments, the growth factor comprises a bone morphogenetic protein.

In certain embodiments, the bone morphogenetic protein is selected from the group consisting BMP-2, BMP-7, BMP-6, BMP-9, and combinations thereof.

In certain embodiments, the bone graft composition further comprises one or more calcium phosphates.

In certain embodiments, the calcium phosphates are selected from the group consisting of hydroxyapatite, tricalcium phosphate, and combinations thereof.

In certain embodiments, the pharmaceutically acceptable carrier comprises a matrix selected from the group consisting of collagens, hydrogels, and combinations thereof.

In certain embodiments, the disclosure relates to a kit comprising a bone morphogenetic protein and the bone graft composition disclosed herein.

In certain embodiments, the disclosure relates to a method of forming bone or cartilage comprising implanting the bone graft composition disclosure herein in a subject under conditions such that bone or cartilage forms.

In certain embodiments, the bone graft composition further comprises a growth factor.

In certain embodiments, the subject has a void in its bony structure and the method comprises implanting the bone graft composition in the void.

In certain embodiments, the bony structure is selected from the group consisting of an extremity, maxilla, a mandible, a pelvis, a spine, a cranium, or a combination thereof.

In certain embodiments, the method comprises implanting the bone graft composition between two vertebrae of the subject to grow bone between the vertebrae.

In certain embodiments, the disclosure relates to a method of preventing or treating a bone fracture comprising administering a pharmaceutical composition comprising a 2,4-diamino-1,3,5-triazine derivative or salt thereof to a subject at risk for, exhibiting symptoms of, or diagnosed with a bone fracture.

In certain embodiments, the pharmaceutical composition further comprises a growth factor.

In certain embodiments, the disclosure relates to a method of preventing or treating a bone degenerative disease comprising administering a pharmaceutical composition comprising a 2,4-diamino-1,3,5-triazine derivative or pharmaceutically acceptable salt thereof to a subject at risk for, exhibiting symptoms of, or diagnosed with a bone degenerative disease.

In certain embodiments, the bone degenerative disease is selected from the group consisting of osteoporosis, osteitis deformans, bone metastasis, multiple myeloma, primary hyperparathyroidism, and osteogenesis imperfecta.

In certain embodiments, the pharmaceutical composition further comprises a growth factor.

Figure 15:
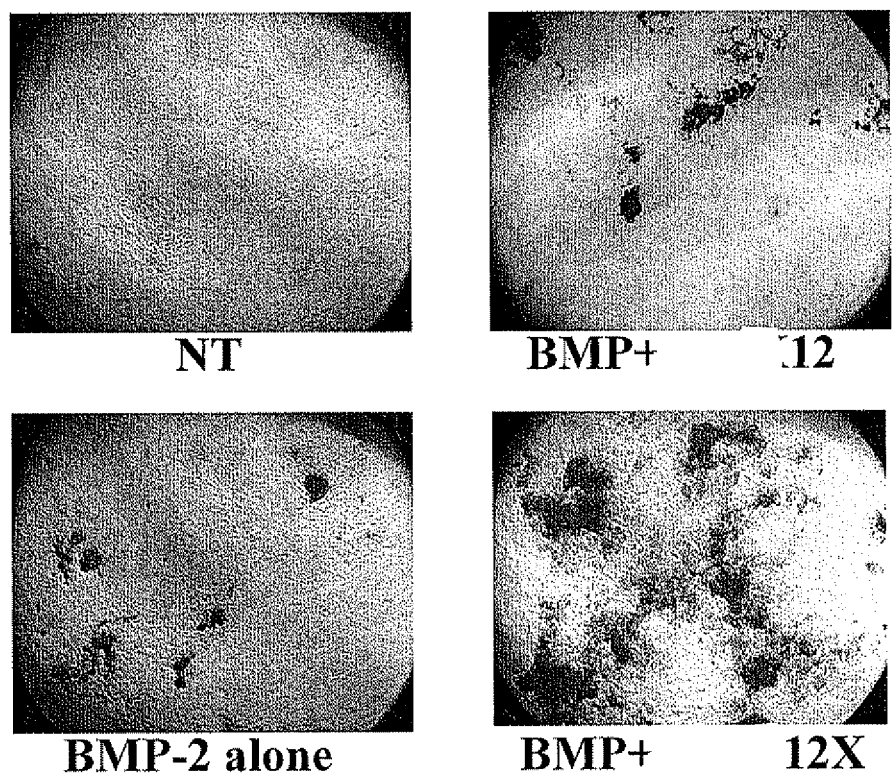

FIG. 15 shows data on the induction of mineralization in ROB cells.

Figure 16:
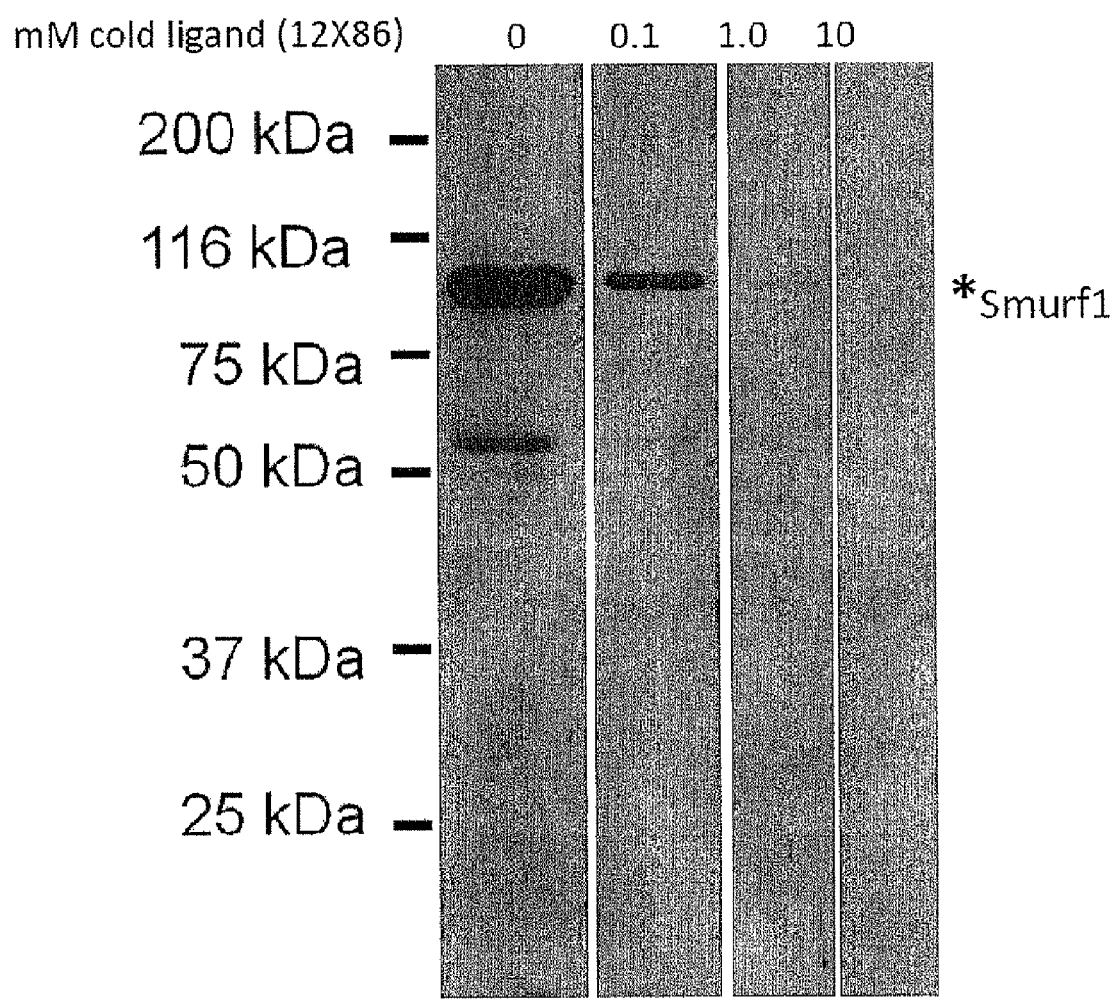
Figure 17A:
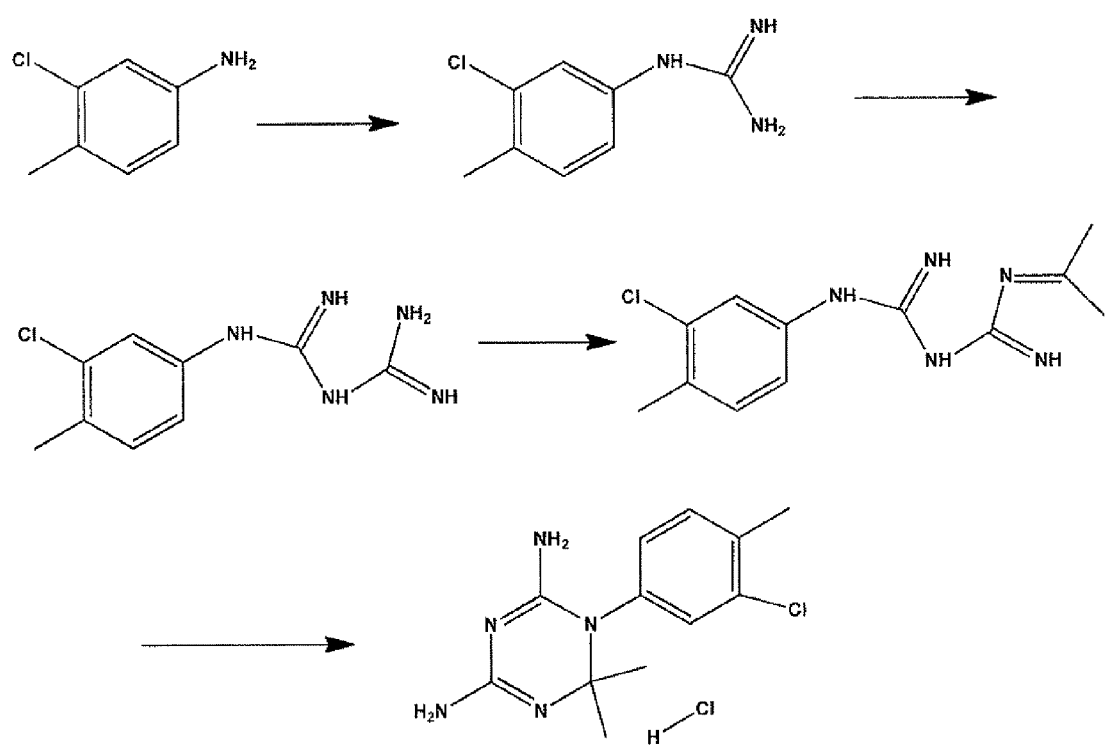
Figure 17B:
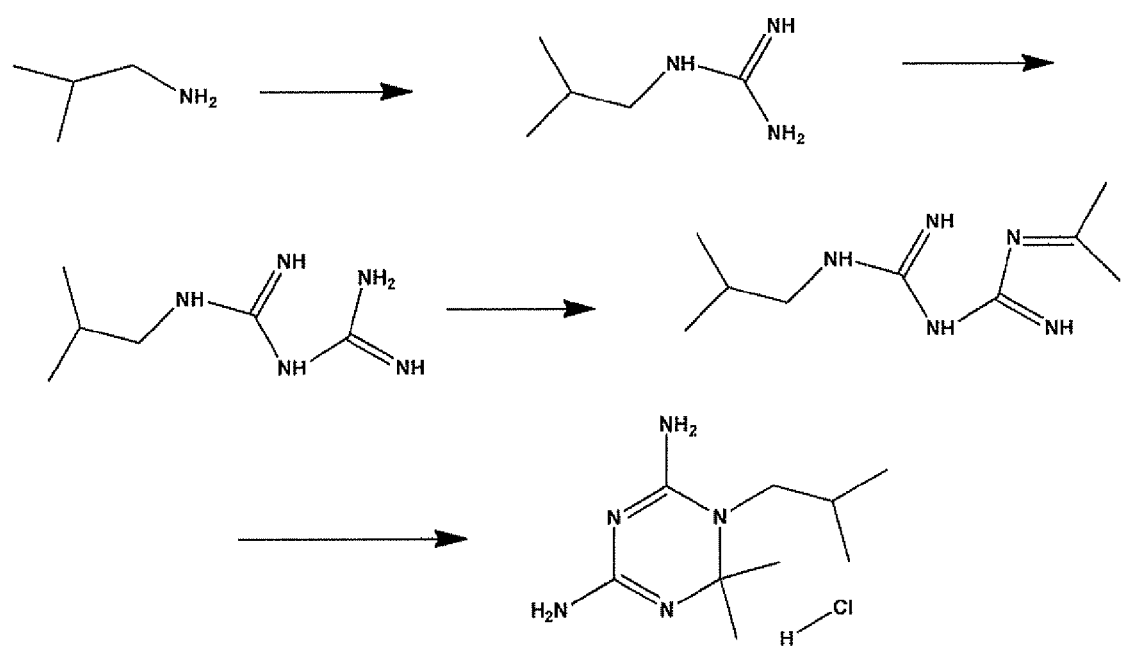
Figure 17C:
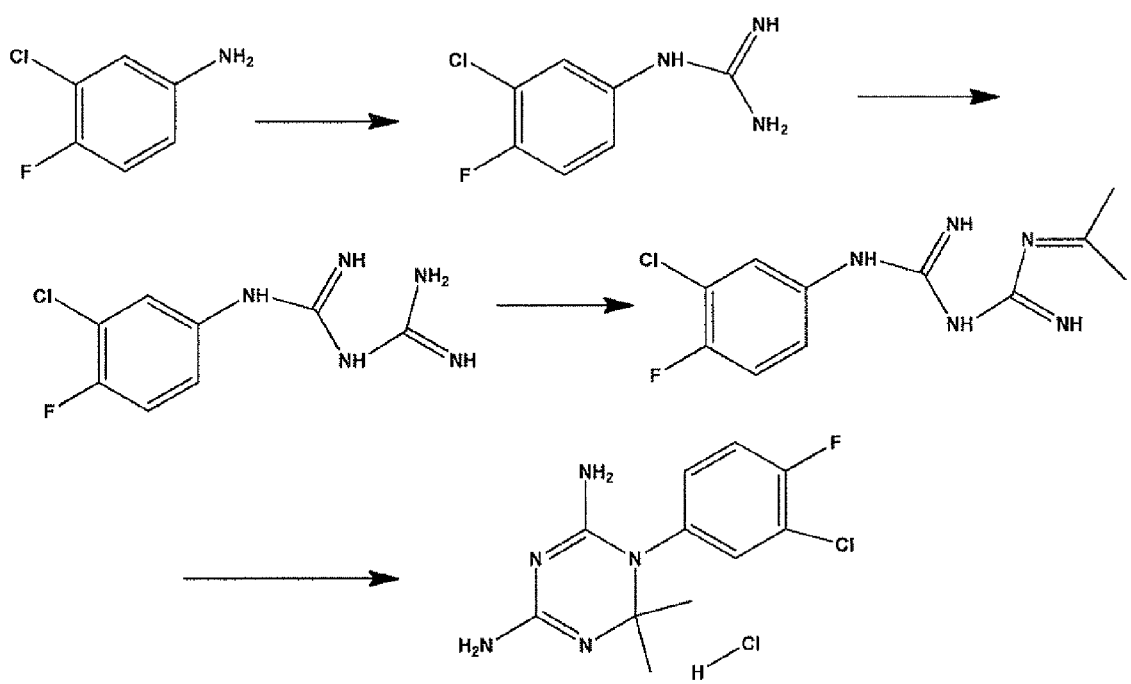
Figure 17D:
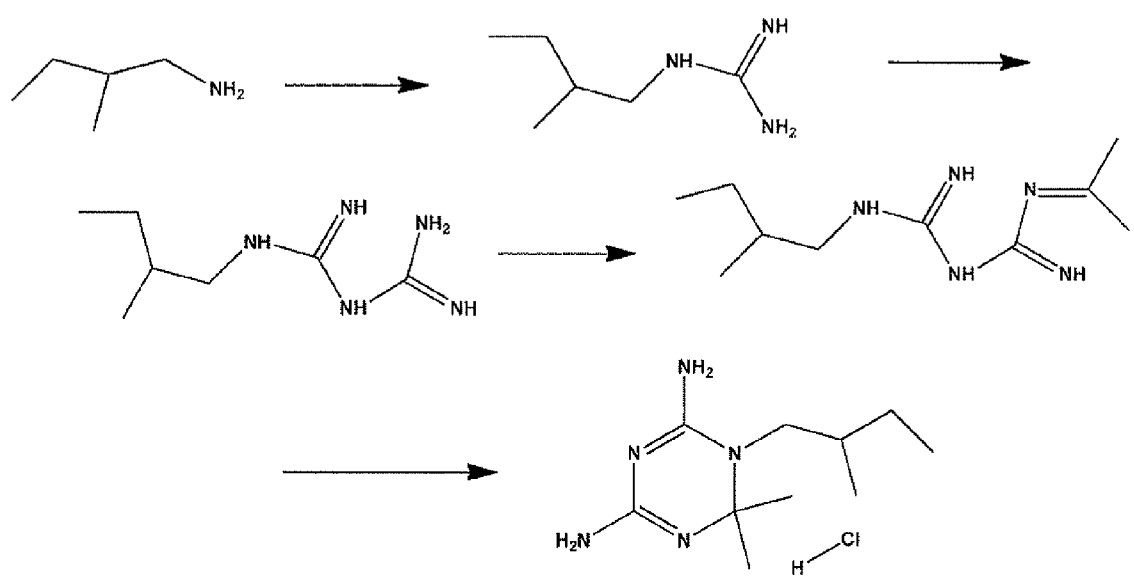

FIG. 16 shows a gel related to homologous binding competition with ligand blotting of purified Smurf1 with unlabeled 12X-86 and 12X-86-I$^{125}$.

FIGS. 17A to D illustrate the schematic synthetic preparation routes of certain embodiments. Substitution of appropriate starting materials may be used to prepare derivates that are not commercially available.

DETAILED DISCUSSION

Terms

"Ossification" refers to the process of laying down new bone by cells called osteoblasts. The term includes the growth in healing bone fractures treated by cast or by open reduction and stabilization by metal plate and screws. Ossification can also result in the formation of bone tissue in an extraskeletal location.

The term "bone morphogenetic protein" or "BMP" refers to any one of the family of growth factors or fragments thereof with the ability to induce the formation of bone and/or cartilage. The BMP receptors are typically serine-threonine kinases. It is not intended that BMP refer to any particular protein sequence and may or may not have certain glycosylation patterns attached thereto provided that the molecule has sufficient structural homology to any one of the known BMPs described below and retains some functional ability to promote bone growth, cartilage growth, or osteoblast differentiation. BMPs may be isolated from natural or non-natural sources, such as, but not limited to, recombinant or synthetic methods. References to BMPs generally or a specific BMP, e.g., BMP-2, includes recombinant or synthetically isolated versions unless otherwise provide for herein. Combinations of BMPs are contemplated. BMP-2 is known to induce bone and cartilage formation and play a role in osteoblast differentiation. BMP-3 is known to induce bone formation. BMP-4 is known to regulate the formation of teeth, limbs and bone from mesoderm and play a role in fracture repair. BMP-5 is known to function in cartilage development. BMP-6 is known to play a role in joint integrity and bone formation/repair. BMP-7 and BMP-9 are known to play a role in osteoblast differentiation. BMP-1 is a known metalloprotease that acts on procollagen I, II, and III and is involved in cartilage development.

As used herein, the term "derivative" refers to a structurally similar compound that retains sufficient functional attributes of the identified analogue. A derivative of 2,4-diamino-1,3,5-triazine derivatives may be compounds, such as 2,4-diamino-6-vinyl-1,3,5-triazine or compound 12X: 1-(4-chlorophenyl)-4,6-diamino-1,2-dihydro-2,2-dimethyl-1,3,5-triazine. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxy group. The derivative may be a prodrug. Derivatives can be prepare by any variety of synthetic methods or appropriate adaptations presented in synthetic or organic chemistry text books, such as those provide in March's Advanced Organic Chemistry Reactions, Mechanisms, and Structure, Wiley, 6th Edition (2007) Michael B. Smith or Domino Reactions in Organic Synthesis, Wiley (2006) Lutz F. Tietze.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "calcium phosphate(s)" refers to minerals containing calcium ions together with orthophosphates, metaphosphates or pyrophosphates and optionally hydroxide ions. Tricalcium phosphate is a calcium phosphate with formula $Ca_3(PO_4)_2$. The common mineral apatite has the basic formula $Ca_5(PO_4)_3X$, where X is a ion, typically a halogen or hydroxide ion, or a mixture. Hydroxyapatite refers to apatite where X is mainly hydroxide ion.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH3).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C═O)alkyl).

"Alkylsulfonyl" refers to an alkyl as defined above attached through a sulfonyl bridge (i.e., —S(═O)$_2$alkyl) such as mesyl and the like, and "Arylsulfonyl" refers to an aryl attached through a sulfonyl bridge (i.e., —S(═O)$_2$aryl).

"Alkylsulfamoyl" refers to an alkyl as defined above attached through a sulfamoyl bridge (i.e., —S(═O)$_2$NHalkyl), and an "Arylsulfamoyl" refers to an alkyl attached through a sulfamoyl bridge (i.e., —S(═O)$_2$NHaryl).

"Alkylsulfinyl" refers to an alkyl as defined above with the indicated number of carbon atoms attached through a sulfinyl bridge (i.e. —S(═O)alkyl).

The terms "halogen" and "halo" refer to fluorine, chlorine, bromine, and iodine.

The term "bone graft composition" refers to materials that are substantially physiologically compatible when residing in bone area, void, or exterior site. In certain embodiments, the bone graft composition may be a bone graft matrix such as a collagen sponge or a mixture of polymers and salts.

Compounds

In certain embodiments, the disclosure relates to 2,4-diamino-1,3,5-triazine derivatives having formula I:

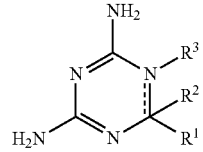

Formula I or a salt thereof, wherein if ---- is a single bond then $R^3$ is carbocyclyl, aryl, or heterocyclyl wherein $R^3$ is optionally substituted with one or more the same or different $R^4$, or $R^3$ is alkyl, phenyl, benzyl, carbocyclyl, aryl, or heterocyclyl wherein $R^3$ is optionally substituted with one or more the same or different $R^4$, $R^2$ is hydrogen or alkyl, such as methyl, and $R^1$ is hydrogen or alkyl; or if ----, is a double bond then $R^1$ is alkyl, alkenyl, carbocyclyl, aryl, or heterocyclyl wherein $R^1$ is optionally substituted with one or more the same or different $R^4$; and $R^2$ and $R^3$ are absent;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, ---- is a single bond, $R^3$ is alkyl, phenyl, benzyl, carbocyclyl, aryl, or heterocyclyl wherein $R^3$ is optionally substituted with one or more the same or different $R^4$, and $R^1$ and $R^2$ are each the same or different alkyl, such as methyl.

In certain embodiments, $R^1$ and $R^2$ are alkyl.

In certain embodiments, $R^4$ is halogen, alkyl, alkoxy, or hydroxy.

In certain embodiments, $R^4$ is chloro.

In certain embodiments, $R^3$ is phenyl or benzyl wherein $R^3$ is substituted with one or more halogens, alkyl, hydroxy or alkoxy.

In certain embodiments, $R^3$ is 3-chlorophenyl optionally substituted with one or more halogens, alkyl, hydroxy or alkoxy.

In certain embodiments, the 2,4-diamino-1,3,5-triazine derivative has formula I or salts thereof, wherein (A) if ---- is a single bond, then $R^3$ is alkyl, phenyl, benzyl, carbocyclyl, aryl, or heterocyclyl optionally substituted with one or more the same or different $R^4$, $R^2$ is hydrogen or alkyl, and $R^1$ is hydrogen or alkyl; or (B) if ---- is a double bond, then $R^1$ is alkyl, alkenyl, carbocyclyl, aryl, or heterocyclyl optionally substituted with one or more the same or different $R^4$, and $R^2$ and $R^3$ are absent;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$ groups; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In some embodiments, the 2,4-diamino-1,3,5-triazine derivatives have formula I or salts thereof, wherein if ---- is a single bond then $R^3$ is carbocyclyl, aryl, or heterocyclyl wherein $R^3$ is optionally substituted with one or more the same or different $R^4$;

$R^2$ is hydrogen or alkyl, such as methyl, and $R^1$ is hydrogen or alkyl; or if ---- is a double bond then $R^1$ is alkyl, alkenyl, carbocyclyl, aryl, or heterocyclyl wherein $R^1$ is optionally substituted with one or more the same or different $R^4$; and $R^2$ and $R^3$ are absent;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to 2,4-diamino-1,3,5-triazine derivatives having formula IA:

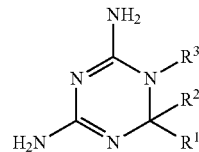

Formula IA or a salt thereof, wherein $R^3$ is alkyl, phenyl, benzyl, carbocyclyl, aryl, or heterocyclyl wherein $R^3$ is optionally substituted with one or more the same or different $R^4$;

$R^2$ is hydrogen or alkyl;

$R^1$ is hydrogen or alkyl;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is halogen, alkyl, alkoxy, or hydroxy.

In certain embodiments, $R^4$ is chloro.

In certain embodiments, $R^3$ is phenyl or benzyl wherein $R^3$ is substituted with one or more halogens, alkyl, hydroxy or alkoxy.

In certain embodiments, $R^3$ is 3-chlorophenyl optionally substituted with one or more halogens, alkyl, hydroxy or alkoxy.

In certain embodiments, $R^1$ and $R^2$ are alkyl.

In certain embodiments, the disclosure relates to 2,4-diamino-1,3,5-triazine derivatives having formula IB:

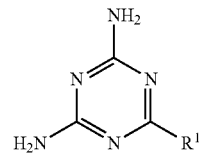

Formula IB or a salt thereof, wherein $R^1$ is alkyl, alkenyl, carbocyclyl, aryl, or heterocyclyl optionally substituted with one or more the same or different $R^4$;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is halogen, alkyl, alkoxy, or hydroxy.

In certain embodiments, $R^1$ is phenyl or benzyl wherein $R^1$ is substituted with one or more halogens, alkyl, hydroxy or alkoxy.

In certain embodiments, the 2,4-diamino-1,3,5-triazine derivatives have formula II:

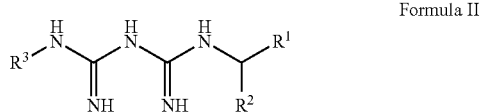

Formula II or a salts thereof wherein $R^1$ is hydrogen or alkyl; $R^2$ is hydrogen or alkyl, such as methyl, and $R^3$ is alkyl, phenyl, benzyl, carbocyclyl, aryl, or heterocyclyl wherein $R^3$ is optionally substituted with one or more the same or different $R^4$;

$R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is halogen, alkyl, alkoxy, or hydroxy.

In certain embodiments, $R^4$ is chloro.

In certain embodiments, $R^3$ is phenyl or benzyl wherein $R^3$ is substituted with one or more halogens, alkyl, hydroxy or alkoxy.

In certain embodiments, $R^3$ is 3-chlorophenyl optionally substituted with one or more halogens, alkyl, hydroxy or alkoxy.

In certain embodiments, $R^3$ is phenyl or benzyl wherein $R^3$ is substituted with one or more halogens, alkyl, hydroxy or alkoxy.

In certain embodiments, $R^1$ and $R^2$ are alkyl.

Evaluations of Compound Activity

Figure 1:
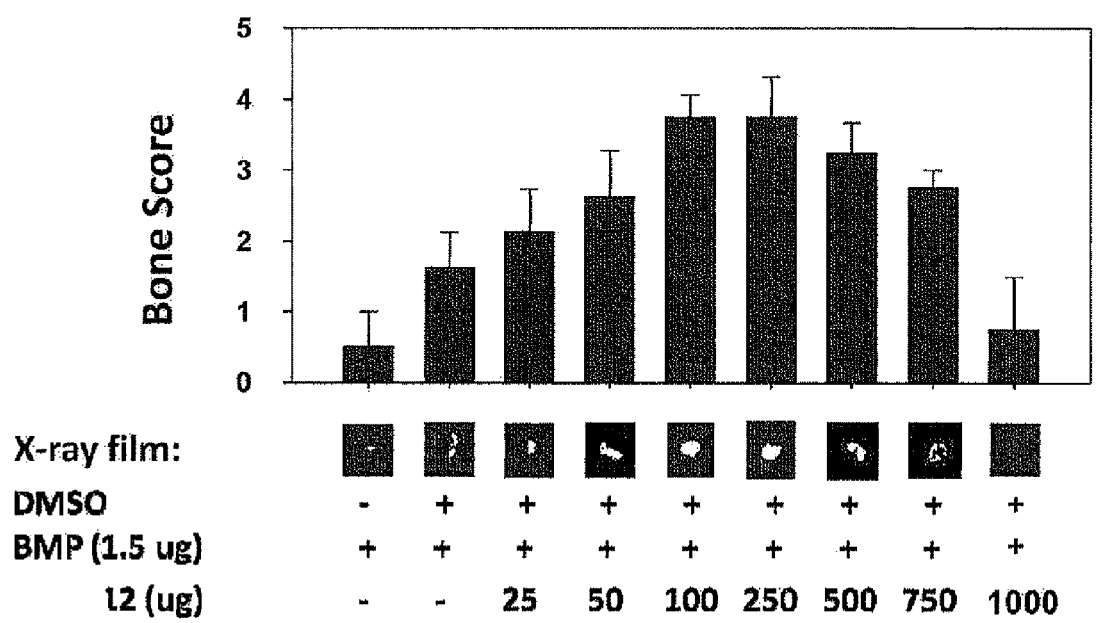
FIG. 1 shows data on ectopic bone induction by compound 12: 2,4-diamino-6-vinyl-1,3,5-triazine and BMP-2.
Figure 2:
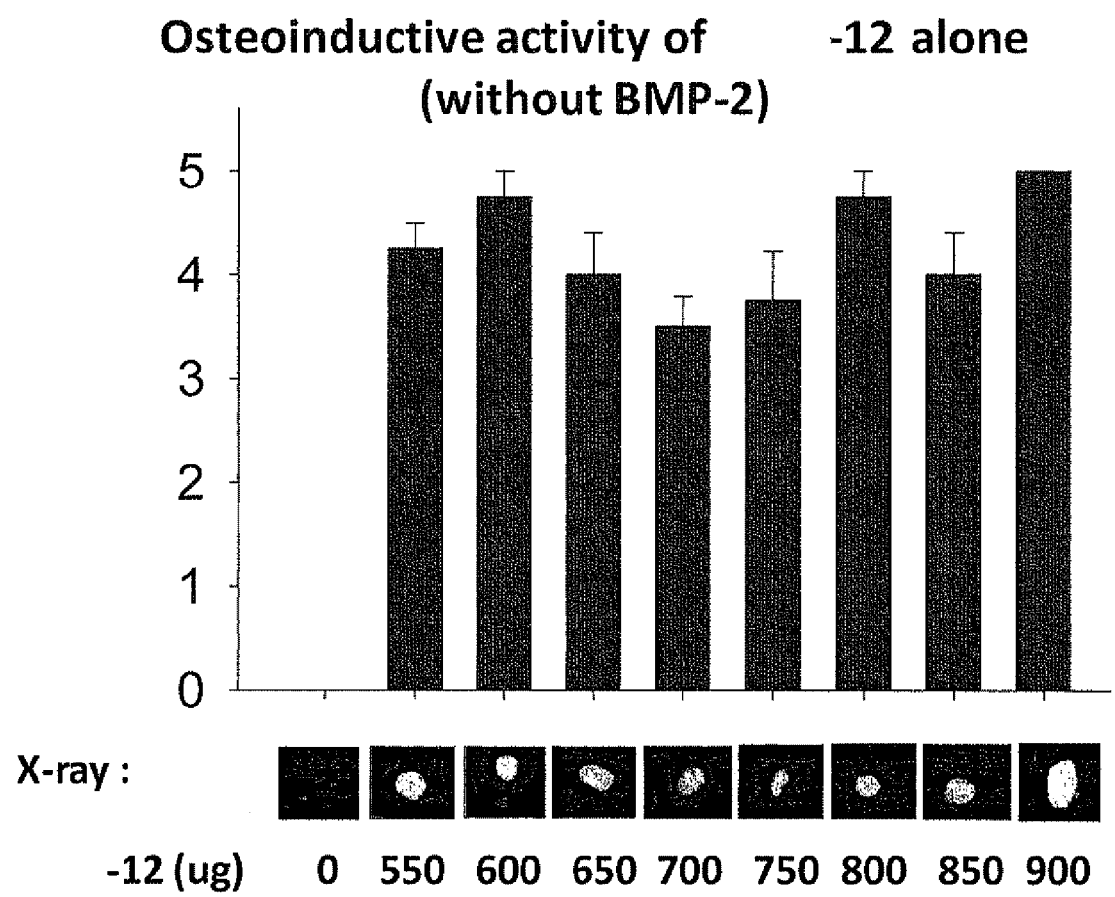
FIG. 2 shows data on ectopic bone induction by compound 12: 2,4-diamino-6-vinyl-1,3,5-triazine without BMP-2.
Figure 3:
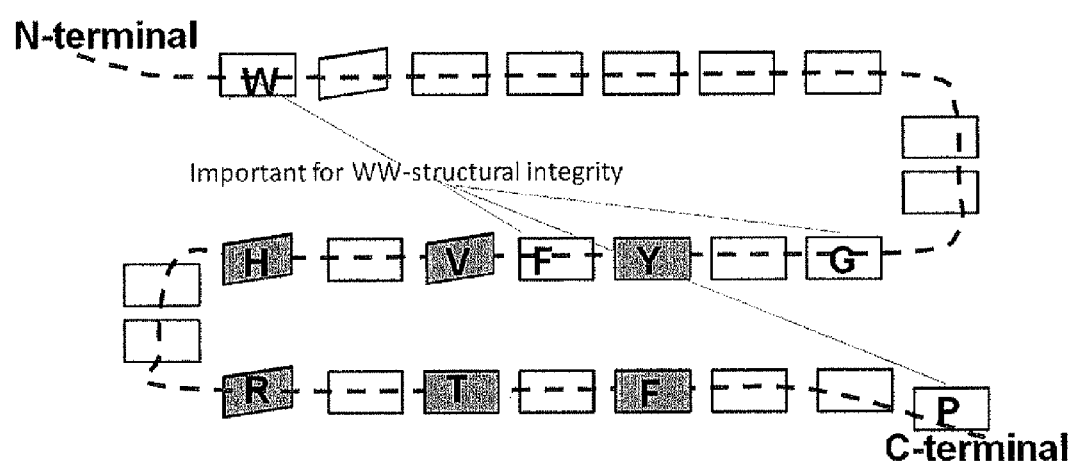
FIG. 3 illustrates important amino acid residues in WW2 domain of Smurf1. Residues labeled in white boxes are important for structural integrity of beta sheets in the WW-domain. Residues labeled in pink boxes are involved in natural target protein interaction commonly in WW-domains. Residues labeled in green boxes are unique to Smurf1 interaction and confer binding specificity to its natural targets.
Figure 4:
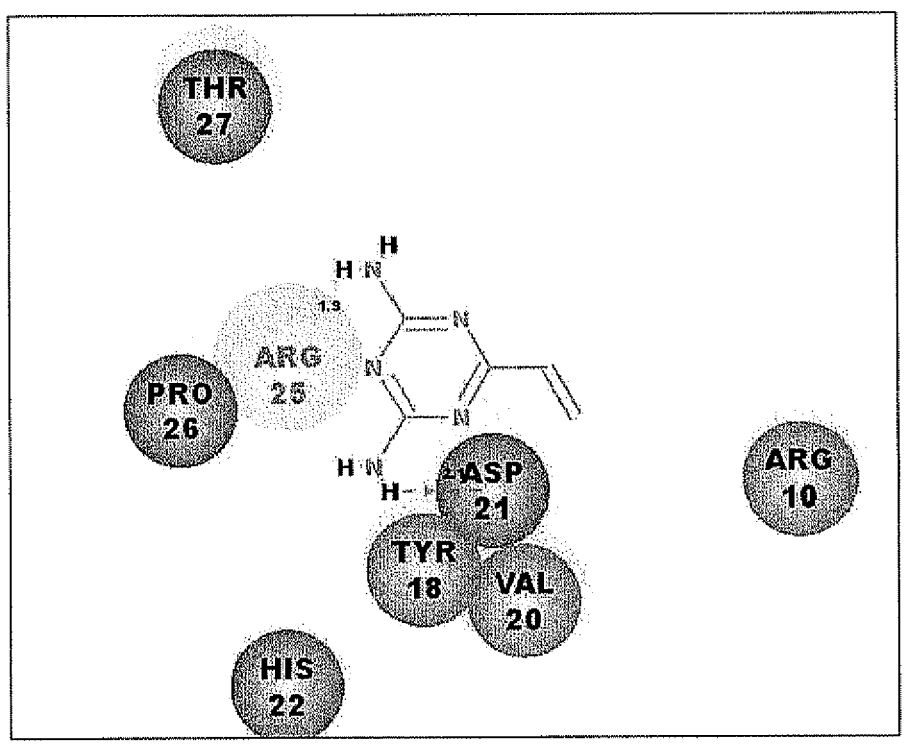
FIG. 4 shows the energetically favored 2D interaction map of compound-12-WW2-Molecule. CDOCKING was performed using compound-12 and 6-key residues in Smurf1-WW2 domain (Y-V-H-R-T-F) as receptor binding sites. In a ligand pose the residues, Asp21 and Arg25, participate in H-bonding.

Potentiating effect of compound 12; (2,4-diamino-6-vinyl-1,3,5-triazine) in BMP-induced in vivo bone-formation in rat model was evaluated (see FIG. 1). Compound 12 is capable of inducing bone-formation without any BMP-2 in rat model (see FIG. 2). The compound is selected by virtual screening of chemical databases using the Ludi docking and scoring functions. FIG. 3 shows the key amino acid residues of Smurf1-WW2 domain involved in determining the unique beta sheet (secondary structure) as well as the residues required for common ligand interaction (residues labeled pink, FIG. 3). Important amino acid residues for Smurf1-specific interaction to the natural target proteins were also identified (residues labeled in green box, FIG. 3). The interaction map for compound binding to WW2 domain of Smurf1 is shown in FIG. 4.

Derivatives with desired attributes can be evaluated using the procedure described below. It has been identified that 2,4-diamino-6-vinyl-1,3,5-triazine and compound 12X: 1-(4-chlorophenyl)-4,6-diamino-1,2-dihydro-2,2-dimethyl-1,3,5-triazine potentiate the effects of BMP-2 in inducing transdifferentiation of C2C12 myoblasts into the osteoblastic phenotype. The enhancement of BMP-2 activity by 2,4-diamino-6-vinyl-1,3,5-triazine was characterized by evaluating a BMP-specific reporter activity and by monitoring the BMP-2-induced expression of mRNA for osteocalcin and alkaline phosphatase which are widely accepted marker genes of osteoblast differentiation. The compound enhanced BMP-2-induced activity of alkaline phosphatase and exhibits a dose-dependent activity in inducing osteoblastic differentiation of myoblastic C2C12 cells even when multiple markers of the osteoblastic phenotype were monitored in parallel.

A cell-based method was optimized to monitor BMP-2 induced responses. The mouse-derived C2C12 myoblasts served as an experimentally tractable model system for investigating the molecular basis of transdifferentiation towards the osteoblastic phenotype. One can monitor transcriptional activity driven by activated Smad1 in C2C12 cells in a cell-based assay utilizing a Smad1-specific luciferase reporter plasmid containing a multimerized-GCCG-motif (9 copies). Okada et al. (2009) Cell Biochem Funct. 27: 526-534. The BMP-specific Smad1-driven 9×GCCG reporter construct has been widely used to assay BMP activity in many cell types at a typical concentration of 50-100 ng/ml of BMP-2. To select a sub-optimal dose of BMP-2 for studying the potentiating effect of test compounds, the reporter assay was performed with lower BMP-2 concentrations ranging from 0.25 to 25 ng/ml. A concentration range of BMP-2 required for activating the reporter assay was established. The results from this experiment allowed selection of a sub-optimal dose (1.0 ug/ml) of BMP-2 to assess the potentiating effects to test compounds in subsequent experiments.

Figure 5A:
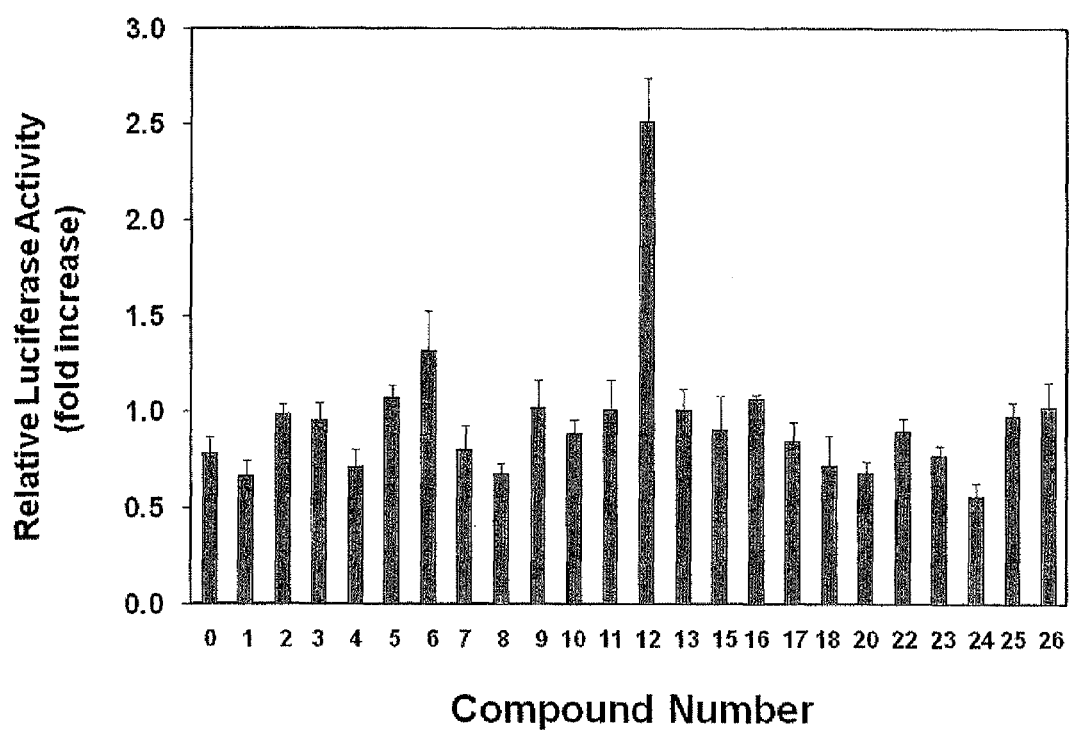
FIGS. 5 A and B shows data on of the efficacy of various compounds to enhance BMP-induced luciferase activity. Relative activities of a representative set of candidate compounds that were selected by virtual screenings were tested in the luciferase reporter assay are shown. Compounds were tested at a concentration of 1.0 ug/ml while BMP-2 was used at 1.0 ng/ml.
Figure 5B:
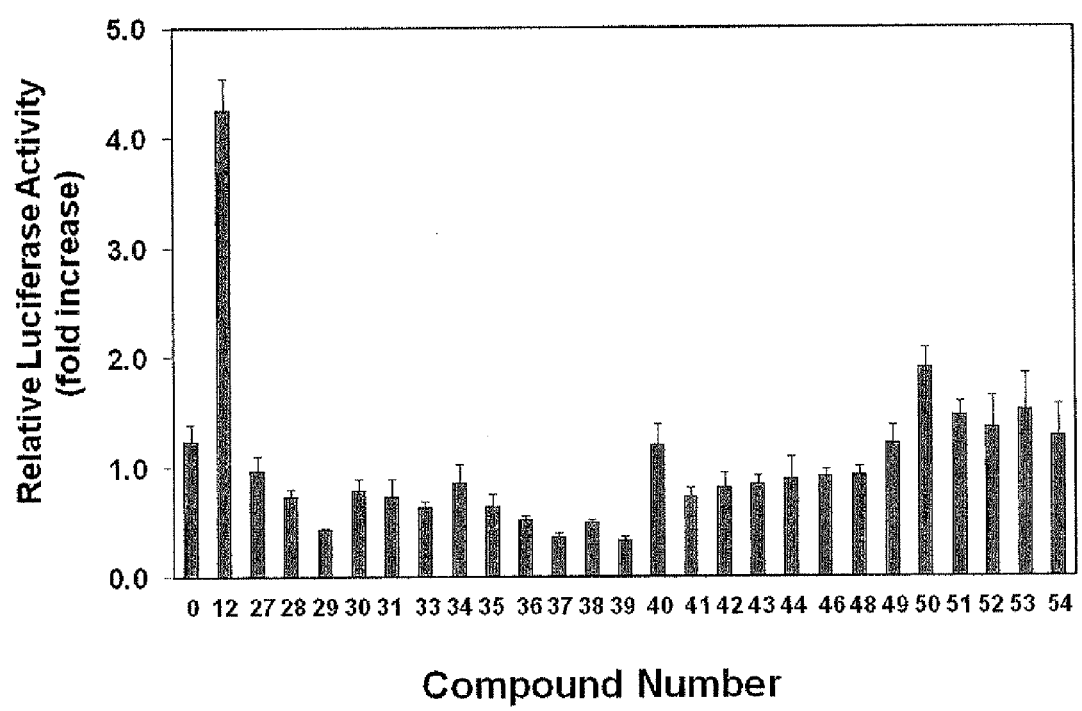

The compound 2,4-diamino-6-vinyl-1,3,5-triazine potentiates BMP-2 induced Smad1-driven luciferase reporter activity. Compounds were tested experimentally for their ability to potentiate BMP-2 activity in our luciferase reporter assay using C2C12 cells (FIGS. 5A and 5B). The solvent dimethylsulfoxide (DMSO) controls showed only basal activity similar to no treatment controls. The DMSO solvent concentration of 0.01% (v/v) was not toxic to cells as determined by cell number, total protein amount, and cell phenotype consistent with the literature. At concentrations higher than 1.5 ug/ml, 2,4-diamino-6-vinyl-1,3,5-triazine caused lifting of some cells from the plates, thus reducing the number of cells at the end of the experiment. Compound 12X: 1-(4-chlorophenyl)-4,6-diamino-1,2-dihydro-2,2-dimethyl-1,3,5-triazine is predicted to have a lower liver toxicity index based on "in silico" ADMET profiling (Discovery Studio 2.5.5, Accelrys, Inc., San Diego, Calif.) of the hepatotoxicity probability (Table 1).

TABLE 1

| Comp. | Formal Name | CDOCKER-Energy (negative value) | Hepatotoxicity Probability |
|---|---|---|---|
| 12 | 6-vinyl-1,3,5-triazine-2,4-diamine | 31.02 | 0.89 |
| 12X | 1-(4-chlorophenyl)-4,6-diamino-1,2-dihydro-2,2-dimethyl-1,3,5-triazine | 19.19 | 0.31 |
| 12X-81 | 1-(3-chloro-4-methylphenyl)-4,6-diamino-1,2-dihydro-2,2-dimethyl-1,3,5-triazine | 20.52 | 0.304 |
| X10 | 1-(2,5-dimethylphenyl)-4,6-diamino-1,2-dihydro-2,2-dimethyl-1,3,5-triazine | 22.07 | 0.225 |
| X13 | 1-(4-chloro-2-methylphenyl)-4,6-diamino-1,2-dihydro-2,2-dimethyl-1,3,5-triazine | 20.48 | 0.278 |

Effectiveness of 2,4-diamino-6-vinyl-1,3,5-triazine on potentiating BMP-2 activity was determined over the concentration range from 0.125 to 1.0 ug/ml while keeping the BMP-2 concentration at 1 ng/ml in the luciferase reporter assay. It caused a dose-dependent enhancement of the luciferase activity with an optimum enhancement of 3.8-fold (P<0.05) observed at a concentration of 1.0 μg/ml when compared to BMP-2 alone. The $EC_{50}$ value of 2.6 uM was calculated from the Hill plot. The $EC_{50}$ value was generated from fitted curves by solving for x-intercept at the 50% activity level of the Y-intercept. After assay optimization, which included determining optimal BMP-2 concentration, plating density of cells, and compound incubation time, the promoter assay was shown to display the dynamic range and reproducibility required for a screening assay.

Figure 6:
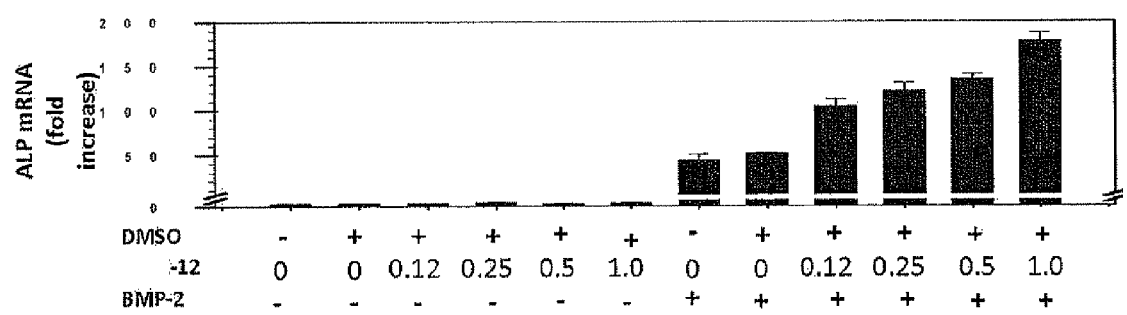
FIG. 6 shows data of potentiation of BMP-2-induced ALP mRNA levels with compound 12.

BMP-2 induced alkaline phosphatase and osteocalcin mRNA levels are enhanced by 2,4-diamino-6-vinyl-1,3,5-triazine. Effectiveness of 2,4-diamino-6-vinyl-1,3,5-triazine was determined over the concentration range from 0.125 to 1.0 ug/ml while keeping the BMP-2 concentration constant at 20 ng/ml by determining alkaline phosphatase mRNA levels (FIG. 6). It caused a dose-dependent increase in the BMP-induced alkaline phosphatase mRNA level with the maximal 3.5-fold increase (P<0.05) compared to BMP-2 alone. BMP-2 alone induced a 43-fold or 51-fold increase in alkaline phosphatase mRNA in the absence or the presence of DMSO (0.01%), respectively, when compared to the 'no treatment' control.

Figure 9:
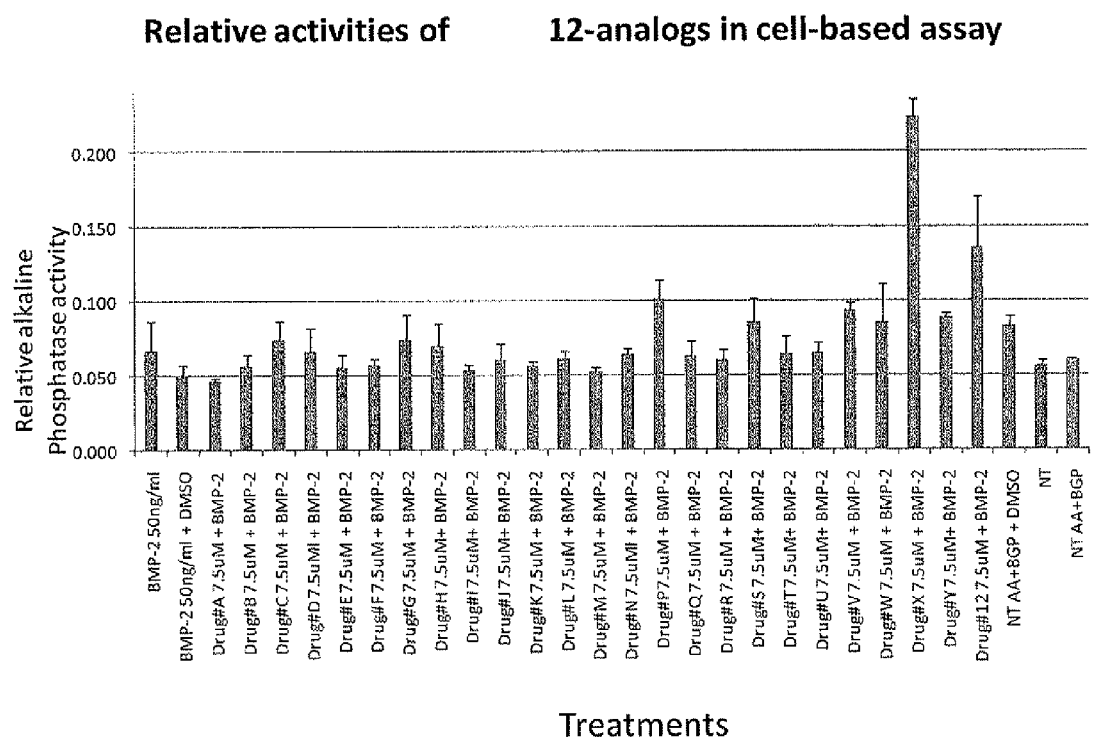
FIG. 9 shows data on the activity of 2,4-diamino-1,3,5-triazine derivatives in promoting BMP-induced of alkaline phosphatase activity. Compound A is 2,4-diamino-6-phenyl-1,3,5-triazine, B is 2-Chloro-4,6-diamino-1,3,5-triazine, C is 6-methyl-1,3,5-triazine-2,4-diamine, D is 2,4-diamino-1,3, 5-triazine, E is 2,4-diamino-6-(2,3-xylyl)-1,3,5-triazine, F is 2,4-diamino-6-(m-tolyl)-1,3,5-triazine, G is 2,4-diamino-6-isobutyryl-1,3,5-triazine, H is 2,4-diamino-6-phenylacetyl-1,3,5-triazine, I is 4,6-diamino-2-hydroxy-1,3,5-triazine, J is 2-chloro-4,6-bis(ethylamino)-1,3,5-triazine, K is 4,6-dimethyl-1,3,5-triazin-2-amine, L is 6-methyl-1,3,5-triazine-2, 4-diamine, M is 2,4-Diamino-6-(2-fluorophenyl)-1,3,5-triazine, N is 2,4,Diamino-6-(3,5-difluorophenyl)-1,3,5-triazine, P is 2,4-diamino-6-(3-fluorophenyl)-1,3,5-triazine, Q is 2,4-diamino-6-(4-bromophenyl)-1,3,5-triazine, R is 6-(4-chlorophenyl)-1,3,5-triazine-2,4-diamine, S is 2,4-diamino-6-(4-methoxphenyl)-1,3,5-triazine, T is 2,4-diamino-6-(4-methylphenyl)-1,3,5-triazine, U is 2,4-diamino-6-(3-nitrophenyl)-1,3,5-triazine, V is 4,6-diamino-gamma-oxo-1, 3,5-triazine-2-butyric acid, W is 4,6-diamino-gamma-oxo-1,3,5-triazine-2-butyronitrile, X (or compound 12X) is 1-(4-chlorophenyl)-4,6-diamino-1,2-dihydro-2,2-dimethyl-1,3,5-triazine, and compound 12 is 2,4-diamino-6-vinyl-1,3,5-triazine.

Data for additional compounds that are derivatives of compound 12 is provided in FIG. 9. Compound A is 2,4-diamino-6-phenyl-1,3,5-triazine, B is 2-Chloro-4,6-diamino-1,3,5-triazine, C is 6-methyl-1,3,5-triazine-2,4-diamine, D is 2,4-diamino-1,3,5-triazine, E is 2,4-diamino-6-(2,3-xylyl)-1,3,5-triazine, F is 2,4-diamino-6-(m-tolyl)-1,3,5-triazine, G is 2,4-diamino-6-isobutyryl-1,3,5-triazine, H is 2,4-diamino-6-phenylacetyl-1,3,5-triazine, I is 4,6-diamino-2-hydroxy-1,3,5-triazine, J is 2-chloro-4,6-bis(ethylamino)-1,3,5-triazine, K is 4,6-dimethyl-1,3,5-triazin-2-amine, L is 6-methyl-1,3,5-triazine-2,4-diamine, M is 2,4-Diamino-6-(2-fluorophenyl)-1,3,5-triazine, N is 2,4,Diamino-6-(3,5-difluorophenyl)-1,3,5-triazine, P is 2,4-diamino-6-(3-fluorophenyl)-1,3,5-triazine, Q is 2,4-diamino-6-(4-bromophenyl)-1,3,5-triazine, R is 6-(4-chlorophenyl)-1,3,5-triazine-2,4-diamine, S is 2,4-diamino-6-(4-methoxyphenyl)-1,3,5-triazine, T is 2,4-diamino-6-(4-methylphenyl)-1,3,5-triazine, U is 2,4-diamino-6-(3-nitrophenyl)-1,3,5-triazine, V is 4,6-diamino-gamma-oxo-1,3,5-triazine-2-butyric acid, W is 4,6-diamino-gamma-oxo-1,3,5-triazine-2-butyronitrile, 12X is 1-(4-chlorophenyl)-4,6-diamino-1,2-dihydro-2,2-dimethyl-1,3,5-triazine, and Compound 12 is 2,4-diamino-6-vinyl-1,3,5-triazine.

Figure 7:
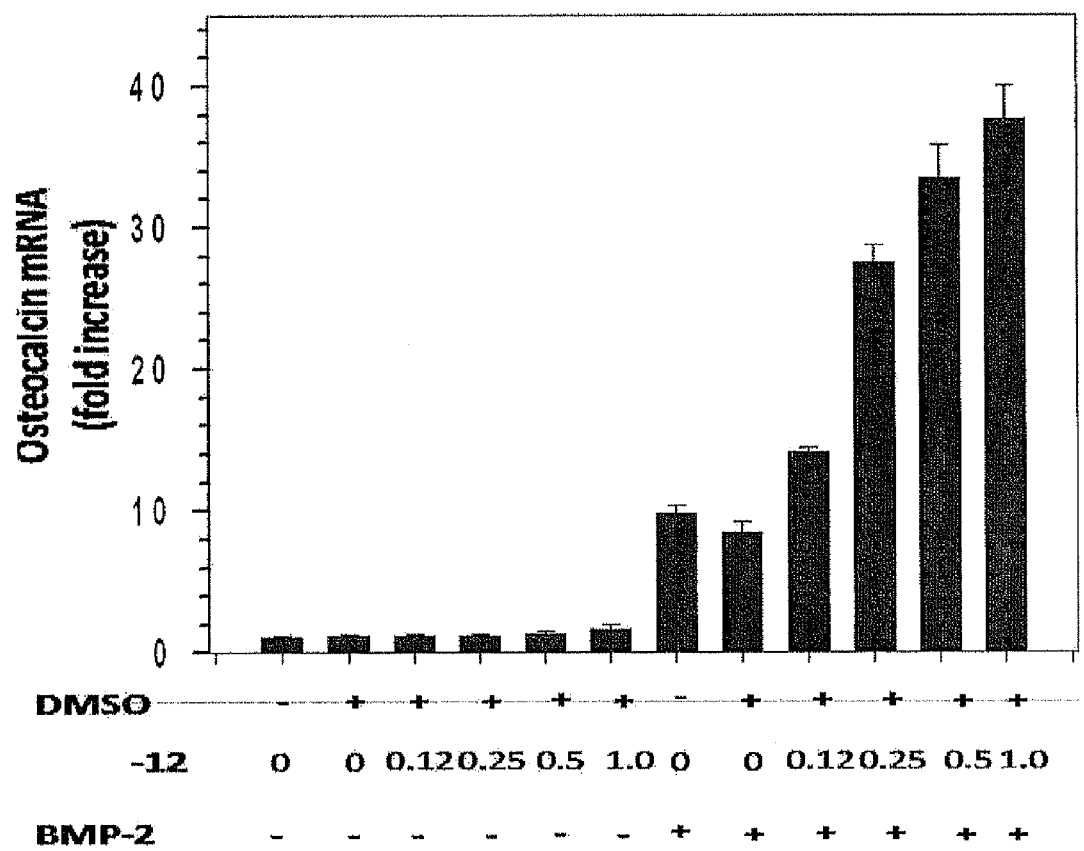
FIG. 7 shows data on potentiation of BMP-2-induced osteocalcin gene expression with compound 12.

The effectiveness of 2,4-diamino-6-vinyl-1,3,5-triazine in increasing BMP-2-induced osteocalcin gene expression was determined over the concentration range from 0.125 to 1.0 ug/ml while keeping the BMP-2 concentration constant at 20 ng/ml. See FIG. 7. The compound caused a dose-dependent increase in the BMP-induced osteocalcin mRNA level with a maximal 4.4-fold increase (P<0.05) compared to BMP-2 alone when observed at a compound concentration of 1.0 μg/ml. BMP-2 alone induced a 9-fold or 7-fold increase in osteocalcin mRNA in the absence or the presence of DMSO (0.01%), respectively, when compared to 'no treatment control'. The compound alone showed no significant effect in the absence of BMP-2. An EC50 value in the range of 1.5 to 5.3 uM was estimated for the expression of both alkaline phosphatase and osteocalcin mRNAs.

Figure 8:
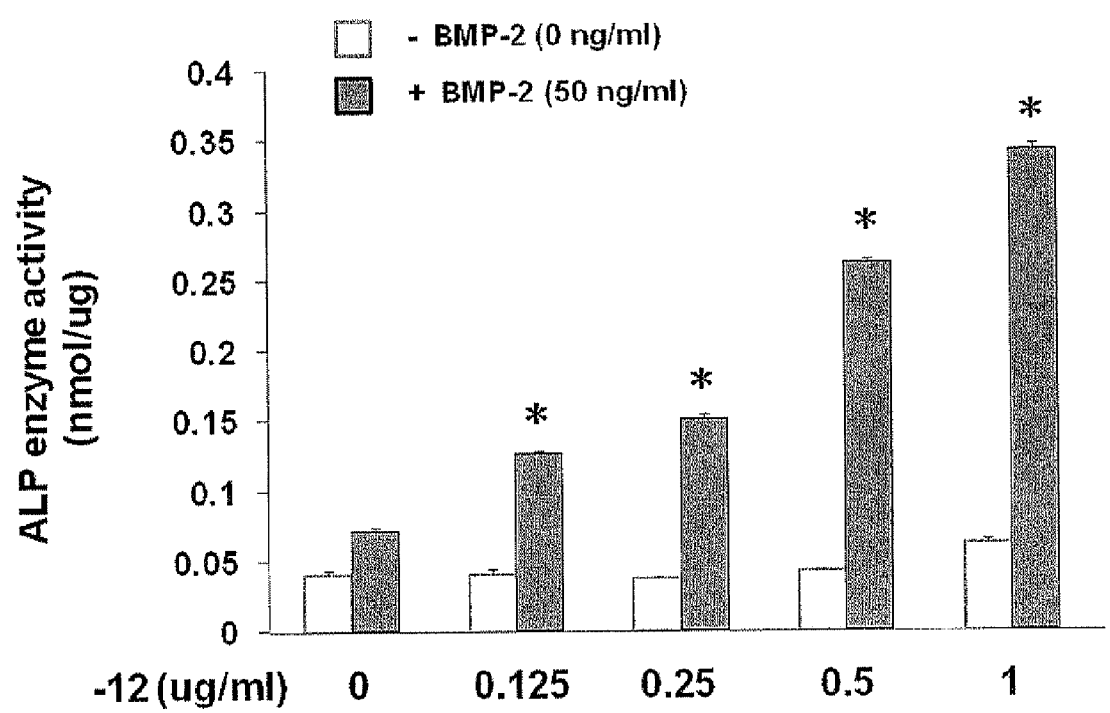
FIG. 8 shows data on potentiation of BMP-induced alkaline phosphatase activity with compound 12.

BMP-2 induced ALP enzyme activity is enhanced by 2,4-diamino-6-vinyl-1,3,5-triazine. In evaluating enhancement of the BMP-induced alkaline phosphatase activity, concentrations of 2,4-diamino-6-vinyl-1,3,5-triazine ranged of 0.125 to 1.0 μg/ml while keeping the BMP-2 concentration constant at 50 ng/ml. The ALP enzyme activity assay demonstrated that the compound dose-dependently enhanced the BMP-2 induced ALP activity (FIG. 8). The peak activity of the maximal 4.8-fold increase (P<0.001) was observed at a compound concentration of 1.0 μg/ml when compared to BMP-2 alone. An EC50 value of 3.7 uM was estimated for the activity of alkaline phosphatase. These results support that 2,4-diamino-6-vinyl-1,3,5-triazine enhances BMP-induced osteoblastic responses in cells.

The compound 2,4-diamino-6-vinyl-1,3,5-triazine elevated the BMP-2-induced response significantly even at a dose of 0.1 μg/ml. The effective dose of compound remained consistent (0.275-1.0 ug/ml) among multiple assays. This suggested that the biological markers in C2C12 cells that we chose to investigate are tightly controlled by the same BMP-signaling pathway. All these studies suggest that the compound or derivatives may be useful in potentiating the BMP-2 responsiveness of cells.

Figure 10:
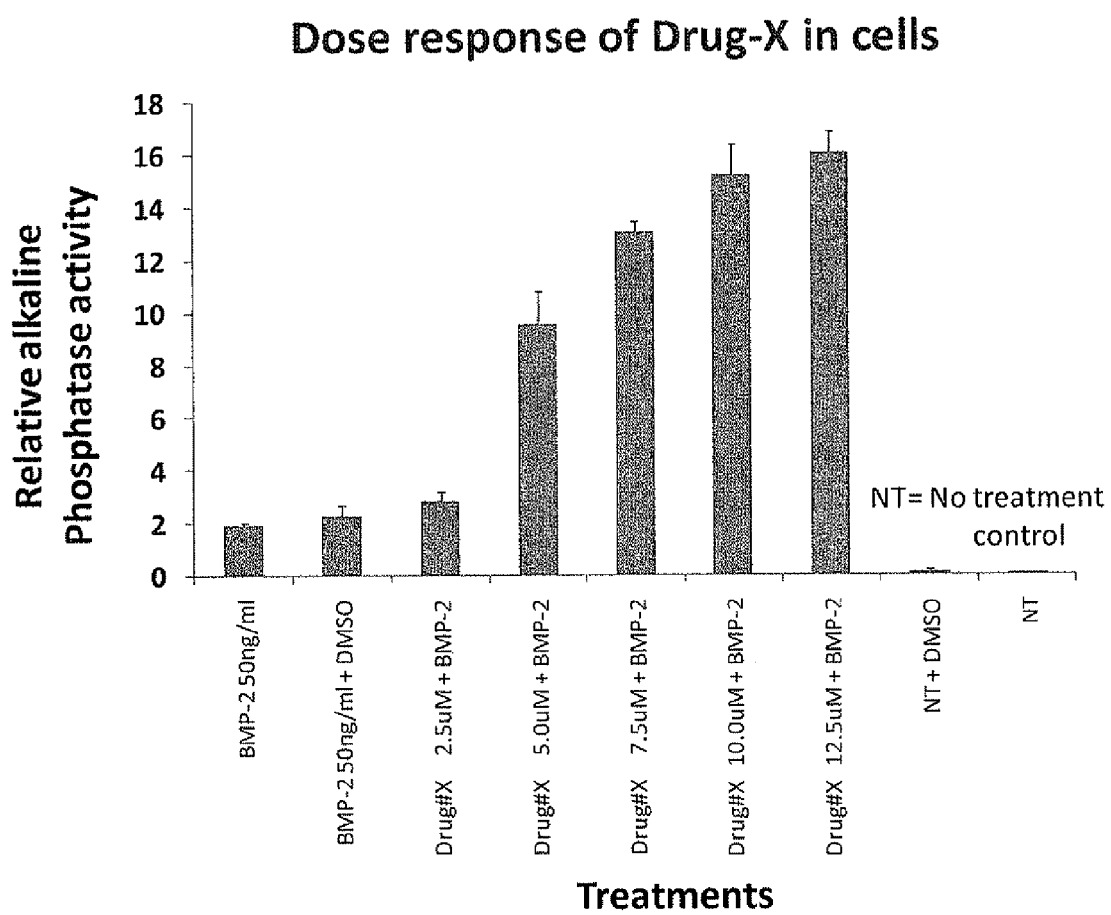
FIG. 10 shows dose response for compound 12X as determined by potentiation of BMP-induced alkaline phosphatase activity.
Figure 11:
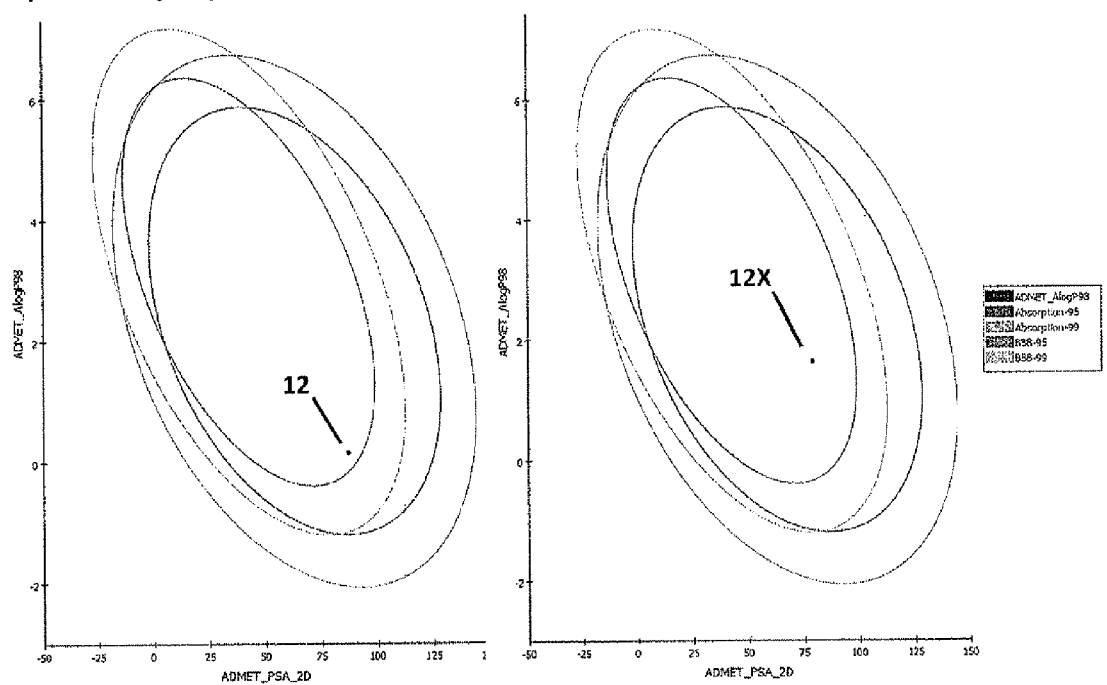
FIG. 11 shows ADMET properties from 12 to 12X as determined by Discovery Studio 2.5.5.version (Accelrys, Inc, San Diego, Calif.).

The in silico ADMET (Absorption, Distribution, Metabolism, Excretion and Toxicity) profiling was performed on compounds using Discovery Studio 2.5.5 (Accelrys, Inc., San Diego, Calif.). The compound 12 showed satisfactory profiles for various ADMET properties except that it showed a higher value (0.89) for hepatotoxicity probability indicating that the compound may be hepatotoxic. In order to find compounds with reduced or no hepatotoxic tendency, compounds were identified on the basis of similarity search using ChemNavigator (Sigma-Aldrich) and Hit2Lead programs. The binding affinity of various compounds was determined by performing in silico CDOCKINGs. Both Compound 12 and Compound 12X showed affinity in binding to same target residues (Asp and Arg) in WW2 domain of Smurf1 mediated by two H-bonds. After screening compounds further with a cell-based alkaline phosphatase assay, compound 12X was identified as a more efficacious derivative (FIG. 9). Compound 12X showed a hepatotoxicity probability value of 0.31 (Table 1). The biological activity of compound 12X by was confirmed determining its activity at various doses as shown in FIG. 10.

Figure 12:
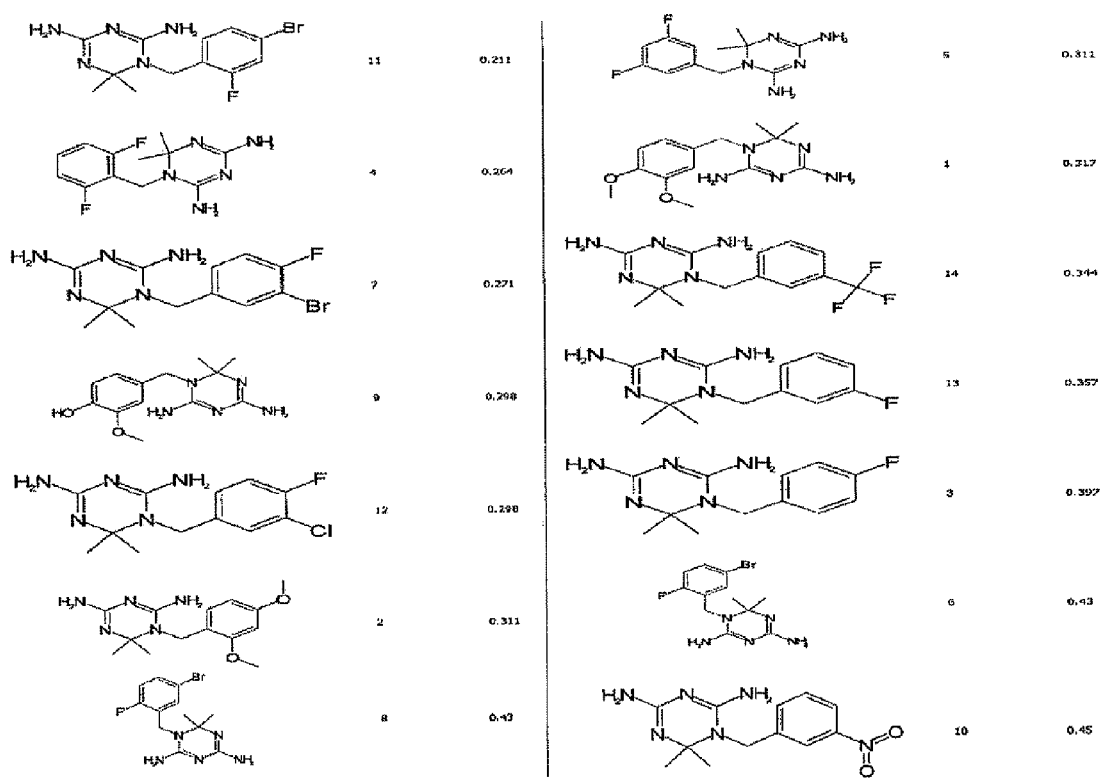
FIG. 12 shows the molecular design of compounds that exhibit osteogenic activity without tendency for toxicity.
Figure 13A:
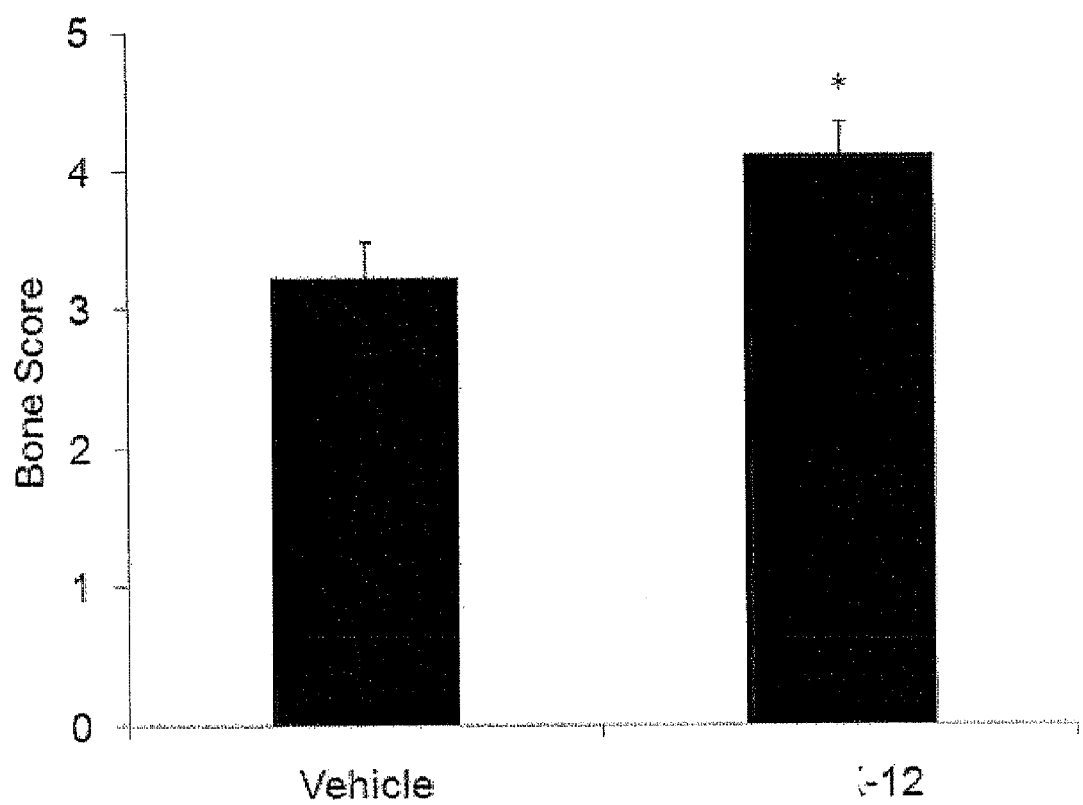
FIGS. 13A to E show data for compound 12 on bone inducing activity in a fracture model using a gap size, bone in gap, and mineralized callus scoring systems.
Figure 13B:
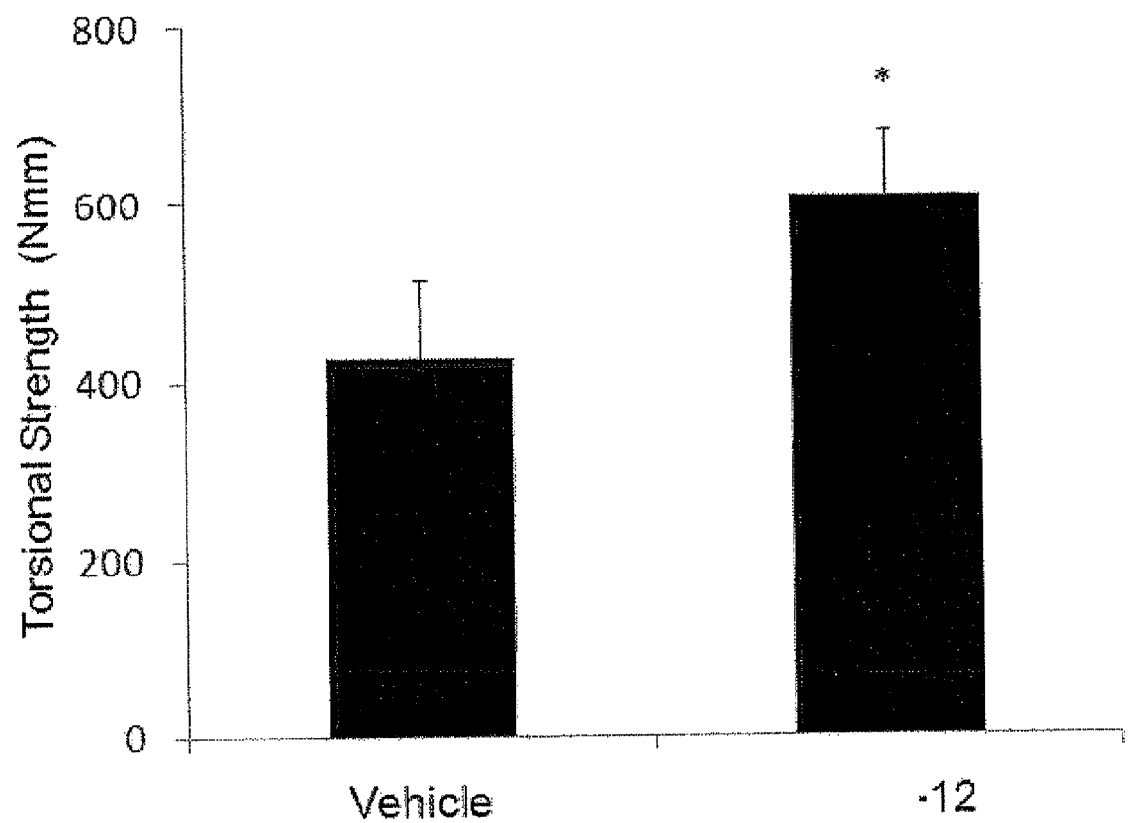
Figure 13C:
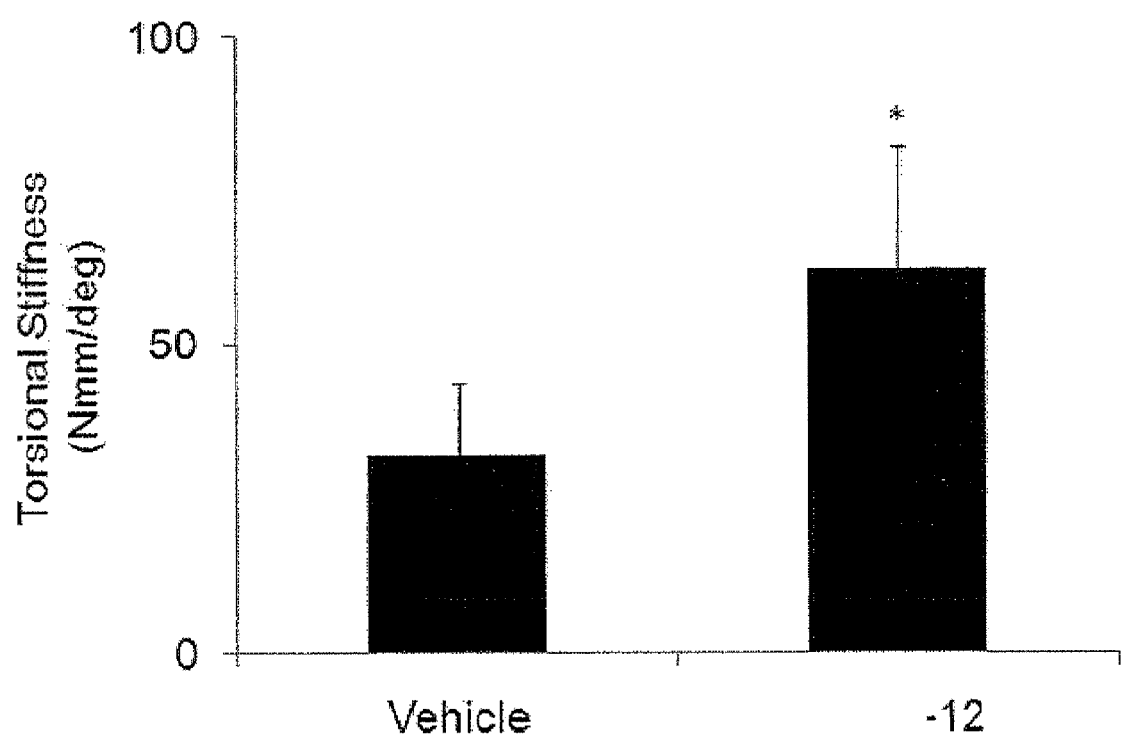
Figure 13D:
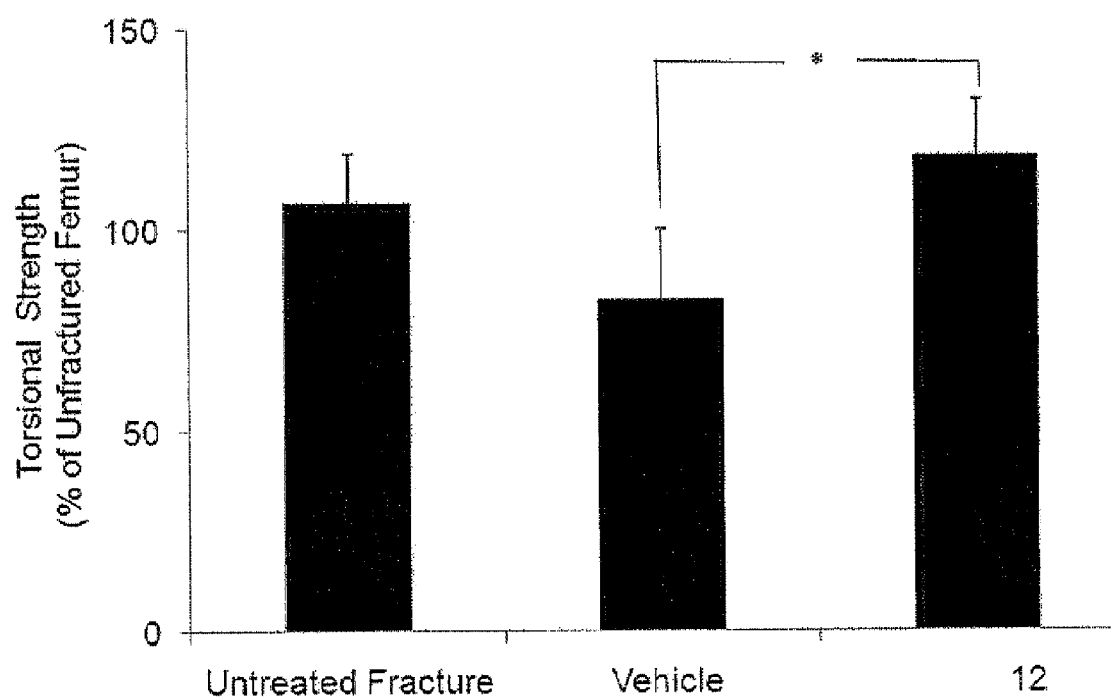
Figure 13E:
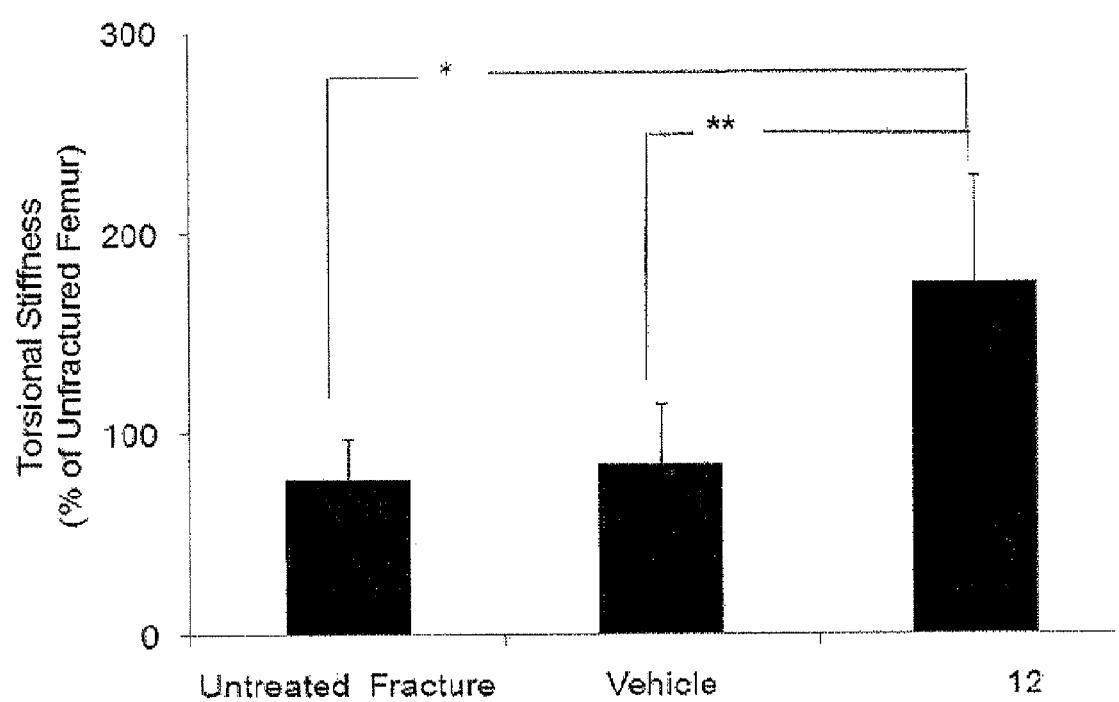
Figure 14A:
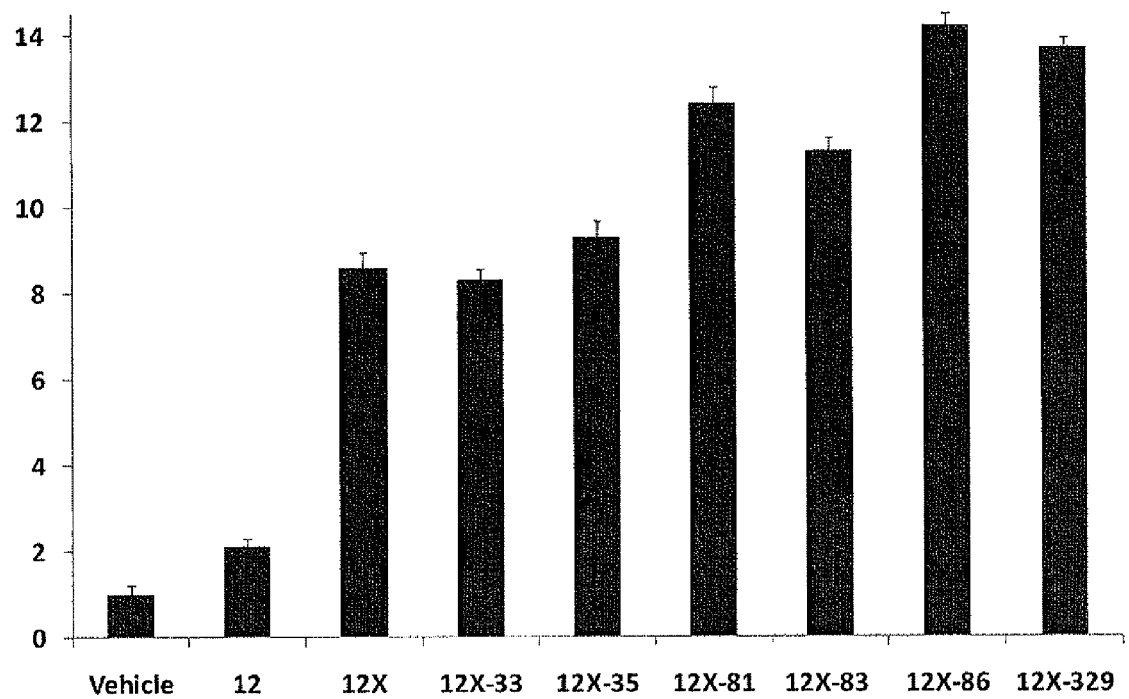
FIGS. 14A and B show data of the fold increase in BMP-induced ALP activity for compounds disclosed herein. Compound 12 is 2,4-diamino-6-vinyl-1,3,5-triazine; 12X is 1-(4-chlorophenyl)-4,6-diamino-1,2-dihydro-2,2-dimethyl-1,3,5-triazine, 12X-33 is 1-(3-chlorophenyl)-4,6-diamino-1, 2-dihydro-2,2-dimethyl-1,3,5-triazine; 12X-35 is 1-(3-chloro-4-methoxyphenyl)-4,6-diamino-1,2-dihydro-2,2-dimethyl-1,3,5-triazine; 12X-81 is 1-(3-chloro-4-methylphenyl)-4,6-diamino-1,2-dihydro-2,2-dimethyl-1,3, 5-triazine; 12X-83 is 1-(3-chloro-5-fluorophenyl)-4,6- diamino-1,2-dihydro-2,2-dimethyl-1,3,5-triazine; 12X-86 is 1-(3-chloro-4-hydroxyphenyl)-4,6-diamino-1,2-dihydro-2,2-dimethyl-1,3,5-triazine; and 12X-329 is 1-(3-chloro-4-fluorophenyl)-4,6-diamino-1,2-dihydro-2,2-dimethyl-1,3,5-triazine.
Figure 14B:
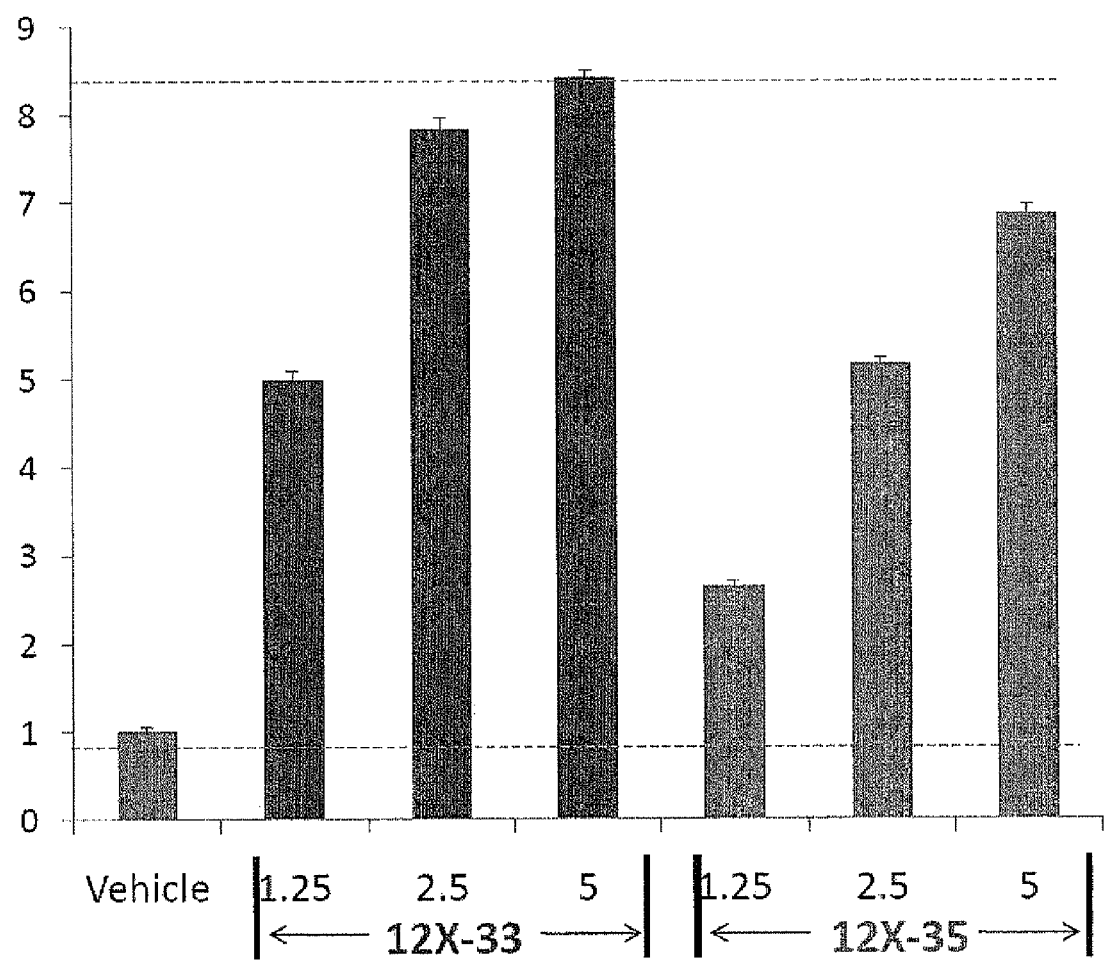

Based on theoretical binding properties, biological activity and in silico ADMET profiles of Compound 12 and Compound 12X, additional computational screenings were performed. These efforts yielded additional compounds (e.g., 12X2, 12X10, and 12X13). These compounds showed no hepatotoxic tendency. Certain of these compounds are shown in FIG. 12.

Growth Factors

In some embodiments, the disclosure relates to the combined use of growth factor(s) and compounds disclosed herein such as 2,4-diamino-6-vinyl-1,3,5-triazine, Compound 12X: 1-(4-chlorophenyl)-4,6-diamino-1,2-dihydro-2,2-dimethyl-1,3,5-triazine or derivatives or salts thereof and one or more growth factors in bone growth applications. Typically, the growth factor is a bone morphogenetic proteins (BMPs), including but not limited to, BMP-1, BMP-2, BMP-2A, BMP-2B, BMP-3, BMP-3b, BMP-4, BMP-5, BMP-6, BMP-7 (OP-1), BMP-8, BMP-8b, BMP-9, BMP-10, BMP-11, BMP-12, BMP-13, BMP-14, BMP-15. BMPs act through specific transmembrane receptors located on cell surface of the target cells.

Non-limiting examples of additional suitable growth factors include osteogenin, insulin-like growth factor (IGF)-1, IGF-II, TGF-beta1, TGF-beta2, TGF-beta3, TGF-beta4, TGF-beta5, osteoinductive factor (OIF), basic fibroblast growth factor (bFGF), acidic fibroblast growth factor (aFGF), platelet-derived growth factor (PDGF), vascular endothelial growth factor (VEGF), growth hormone (GH), growth and differentiation factors (GDF)-5 through 9, and osteogenic protein-1 (OP-1). The growth factors may be isolated from synthetic methods, recombinant sources or may be purified from a biological sample. Preferably the growth factors are obtained from a recombinant technology and for clarity certain embodiments include rhBMP-2, rhBMP-4, rhBMP-6, rhBMP-7, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) Science, 242(4885):1528-1534 hereby incorporated by reference.

In a typical embodiment, a graft composition comprises a matrix, BMP-2, and a compound disclosed herein such as 2,4-diamino-6-vinyl-1,3,5-triazine, 4,6-diamino-1,2-dihydro-2,2-dimethyl-1,3,5-triazine, a derivative or salt thereof or combinations of other growth factors such as GDF-5. In one embodiment, the matrix contains an effective amount of a BMP-2 protein, an rhBMP-2 protein, functional fragments thereof, or combinations thereof. For certain embodiments, the range of concentrations of BMP-2 may be about 1.0 to 4.0 mg/ml and GDF-5 concentrations may be 0.25 to 4.0 mg/ml. Although a graft matrix may be loaded during manufacturing, it is typically loaded just prior to implantation.

The transcription of human BMP-2 is 396 amino acids in length, localized to chromosome 20p12. BMP-2 belongs to the transforming growth factor-beta (TGF-beta) superfamily. The human amino acid sequence BMP-2 is SEQ ID NO:1 shown below Amino acids 38-268 are the TGF-beta propeptide domain, and 291-396 are the TGF-beta family N-terminal domain Amino acids 283-396 are the mature peptide. The mature form of BMP-2 contains four potential N-linked glycosylation sites per polypeptide chain, and four potential disulfide bridges. (SEQ ID NO: 1) 1 MVAG-TRCLLA LLLPQVLLGG AAGLVPELGR RKFAAASSGR PSSQPSDEVL SEFELRLLSM 61 FGLKQRPTPS RDAV-VPPYML DLYRRHSGQP GSPAPDHRLE RAAS-RANTVR SFHHEESLEE 121 LPETSGKTTR RFFFNLS-SIP TEEFITSAEL QVFREQMQDA LGNNSSFHHR INIYEIIKPA 181 TANSKFPVTR LLDTRLVNQN ASR-WESFDVT PAVMRWTAQG HANHGFVVEV AHL-EEKQGVS 241 KRHVRISRSL HQDEHSWSQI RPLLVT-FGHD GKGHPLHKRE KRQAKHKQRK RLKSSCKRHP 301 LYVDFSDVGW NDWIVAPPGY HAFYCHGECP FPLADHLNST NHAIVQTLVN SVNSKIPKAC 361 CVP-TELSAIS MLYLDENEKV VLKNYQDMVV EGCGCR.

In one embodiment, bone morphogenetic protein includes one of the following synthetic peptide fragments of BMP-2: SEQ ID NO: 2 (KIPKASSVPTELSAISTLYLDDD), SEQ ID NO: 3 (CCCCDDDSKIPKASSVPTELSAISTLYL) SEQ ID NO: 4 ($C_{16}H_{31}O$—NH—CCCCGGGSKIPKASSVP-TELSAISTLYL) which may be synthesized by FMOC/tBu solid-phase peptide synthesis.

BMP-7 also belongs to the TGF-beta superfamily. It induces cartilage and bone formation. The amino acid sequence of BMP-7 is SEQ ID NO: 5. (SEQ ID NO: 5) 1 MHVRSLRAAA PHSFVALWAP LFLLRSALAD FSLD-NEVHSS FIHRRLRSQE RREMQREILS 61 ILGLPHRPRP HLQGKHNSAP MFMLDLYNAM AVEEGGGPGG QGFSYPYKAV FSTQGPPLAS 121 LQDSHFLTDA DMVMSFVNLV EHDKEFFHPR YHHREFRFDL SKIPEGEAVT AAEFRIYKDY 181 IRERFDNETF RISVYQVLQE HLGRESDLFL LDSRTL-WASE EGWLVFDITA TSNHWVVNPR 241 HNL-GLQLSVE TLDGQSINPK LAGLIGRHGP QNKQPFM-VAF FKATEVHFRS IRSTGSKQRS 301 QNRSKTPKNQ EALRMANVAE NSSSDQRQAC KKHELYVSFR DLG-WQDWIIA PEGYAAYYCE 361 GECAFPLNSY MNAT-NHAIVQ TLVHFINPET VPKPCCAPTQ LNAISVLYFD DSSNVILKKY 421 RNNVVRACGC H Amino acids 1-29 are a potential signal sequence; 30-431 are the prepropeptide, and 293-431 are the mature protein. The mature form of BMP-7 contains four potential N-linked glycosylation sites per polypeptide chain, and four potential disulfide bridges.

Graft Compositions

In some embodiments, the disclosure relates to a graft composition comprising growth factor(s) and 2,4-diamino-6-vinyl-1,3,5-triazine, Compound 12X: 1-(4-chlorophenyl)-4,6-diamino-1,2-dihydro-2,2-dimethyl-1,3,5-triazine or derivatives or salts thereof. In some embodiments, these compositions can be created from polymers, bone granules, and ceramics such as calcium phosphates (e.g. hydroxyapatite and tricalcium phosphate), bioglass, and calcium sulphate.

Bioglass refers to materials of $SiO_2$, $Na_2O$, $CaO$, and $P_2O_5$ in specific proportions. The proportions differ from the traditional soda-lime glasses in lower amounts of silica (typically less than 60 mol %), higher amounts of sodium and calcium, and higher calcium/phosphorus ratio. A high ratio of calcium to phosphorus promotes formation of apatite crystals; calcium and silica ions can act as crystallization nuclei. Some formulations bind to soft tissues and bone, some only to bone, some do not form a bond at all and after implantation get encapsulated with non-adhering fibrous tissue, and others are completely absorbed overtime. Mixtures of 35-60 mol % $SiO_2$, 10-50 mol % CaO, and 5-40 mol % $Na_2O$ bond to bone and some formulations bond to soft tissues. Mixtures of >50 mol % $SiO_2$, <10 mol % CaO, <35 mol % $Na_2O$ typically intigrate within a month. Some CaO may be replaced with MgO and some $Na_2O$ may be replaced with $K_2O$. Some CaO can be replaced with $CaF_2$.

In some embodiments, the disclosure relates to a graft composition comprising growth factor(s) and compounds disclosed herein such as 2,4-diamino-6-vinyl-1,3,5-triazine, Compound 12X: 1-(4-chlorophenyl)-4,6-diamino-1,2-dihydro-2,2-dimethyl-1,3,5-triazine or derivatives or salts thereof and/or polysaccharides such as hyaluronate, cellulose or cellulose derivatives such as, but not limited to, hydroxypropyl cellulose, methyl cellulose, ethyl cellulose, and carboxymethyl cellulose. Typically, cellulose derivates are used in graft compositions that produce a paste or putty.

In some embodiments, the disclosure relates to a bone graft composition comprising a bone morphogenetic protein and 2,4-diamino-6-vinyl-1,3,5-triazine, Compound 12X: 1-(4-chlorophenyl)-4,6-diamino-1,2-dihydro-2,2-dimethyl-1,3,5-triazine, derivative, or salt thereof and a graft matrix. The matrix is typically a polymer designed to hold bone compatible salts, such as calcium phosphates, for replacement during bone growth. An example is a bovine Type I collagen embedded with biphasic calcium phosphate granules. Optionally, matrix compositions may also include one or more agents that support the formation, development and growth of new bone, and/or the remodeling thereof. Typical examples of compounds that function in, such a supportive manner include extracellular matrix-associated bone proteins such as alkaline phosphatase, osteocalcin, bone sialoprotein (BSP) and osteocalcin, phosphoprotein (SPP)-1, type I collagen, fibronectin, osteonectin, thrombospondin, matrix-gla-protein, SPARC, and osteopontin.

In certain embodiments, the graft matrix can be made up of a hydrogel polymer. Typically, a hydrogel is made-up of acrylate polymers and copolymers substituted with an abundance of hydrophilic groups, such as terminal hydroxy or carboxyl groups. In certain embodiments, the graft composition is biodegradable. In certain embodiments, the matrix comprises homopolymers and copolymers consisting of gylcolide and lactide. For certain embodiments, the graft composition comprises a matrix of hydroxyethylmethacrylate or hydroxymethylmethyacrylate polymers containing hydroxyapatite in a mineral content approximately that of human bone. Such a composition may also be made with crosslinkers comprising an ester, anhydride, orthoester, amide, or peptide bond. In some embodiments, crosslinkers contain the following polymers: polyethylene glycol (PEG), polylactic acid, polyglycolide or combinations thereof.

In certain embodiments, the graft composition may contain one or more antibiotics and/or anti-inflammatory agents. Suitable antibiotics include, without limitation, nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, timidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

Bone Grafting Methods

Bone grafting is possible because bone tissue, unlike most other tissues, has the ability to regenerate if provided the space into which to grow with appropriate chemical signals. With regard to synthetic grafts, as native bone grows, it typically replaces most or all of the artificial graft material, resulting in an integrated region of new bone. However, with regard to certain embodiments of the disclosure, it is not intended that new bone must remove all artificial material. In addition, with regard to certain embodiments of the disclosure, it is not intended that graft location need contact any other bone of the skeletal system.

In certain embodiments, the disclosure relates to a method of forming bone comprising implanting a graft composition comprising a compound disclosed herein such as 2,4-diamino-6-vinyl-1,3,5-triazine, Compound 12X: 1-(4-chlorophenyl)-4,6-diamino-1,2-dihydro-2,2-dimethyl-1,3,5-triazine, derivatives, or salts thereof, in a subject. In certain embodiments, the disclosure relates to methods of forming bone comprising implanting a graft composition comprising a bone morphogenetic protein and compound(s) disclosed herein, such as 2,4-diamino-6-vinyl-1,3,5-triazine, Compound 12X: 1-(4-chlorophenyl)-4,6-diamino-1,2-dihydro-2, 2-dimethyl-1,3,5-triazine, derivatives, or salts thereof, in a subject. The graft may be the result of a void created by surgical removal or created as a result of an attempt to correct a physical abnormality of a bone, such as but not limited to, cranial bones; frontal, parietal, temporal, occipital, sphenoid, ethmoid; facial bones; mandible, maxilla, palatine, zygomatic, nasal, lacrimal, vomer, inferior nasal conchae; shoulder girdle; scapula or shoulder blade, clavicle or collarbone; in the thorax; sternum, manubrium, gladiolus, and xiphoid process, ribs; in the vertebral column; cervical vertebrae, thoracic vertebrae; lumbar vertebrae; in the arms, humerus, radius, ulna; in the pelvis; coccyx; sacrum, hip bone (innominate bone or coxal bone); in the legs; femur, patella, tibia, and fibula. It is contemplated that the graft may be added for cosmetic purposes, e.g., cheek augmentation. In the case of a broken bone or removal of a bone during surgery, it may be desirable to secure movement of bone structure with a fixation system and remove the system after bone forms in the implanted graft.

With regard to prostheses, it may be desirable to grow bone between existing bone and an implanted device, or in preparation of an implanted device, such as in the case of a hip replacement, knee replacement, and dental implant, i.e., artificial tooth root used to support restorations that resemble a tooth or group of teeth.

In some embodiments, the disclosure relates to three-dimensional structures made of biocompatible and biodegradable bone graft materials in the shape of the bone infused with compositions disclosed herein to promote bone growth. Implants can be used to support a number of prostheses. A typical implant consists of a titanium device. In certain embodiments, the graft compositions disclosed herein contain implants.

With regard to a sinus augmentation or alveolar ridge augmentation, surgery may be performed as an outpatient under general anesthesia, oral conscious sedation, nitrous oxide sedation, intravenous sedation or under local anesthesia. Bone grafting is used in cases where there is a lack of adequate maxillary or mandibular bone in terms of depth or thickness. Sufficient bone is needed in three dimensions to securely integrate with the root-like implant. Improved bone height is important to assure ample anchorage of the root-like shape of the implant.

In a typical procedure, the clinician creates a large flap of the gingiva or gum to fully expose the bone at the graft site, performs one or several types of block and onlay grafts in and on existing bone, then installs a membrane designed to repel unwanted infection-causing bacteria. Then the mucosa is carefully sutured over the site. Together with a course of systemic antibiotics and topical antibacterial mouth rinses, the graft site is allowed to heal. The bone graft produces live vascular bone and is therefore suitable as a foundation for the dental implants.

In certain embodiments, the disclosure relates to methods of performing spinal fusion using compositions disclosed herein. Typically this procedure is used to eliminate the pain caused by abnormal motion of the vertebrae by immobilizing the vertebrae themselves. Spinal fusion is often done in the lumbar region of the spine, but the term is not intended to be limited to method of fusing lumbar vertebrae. Patients desiring spinal fusion may have neurological deficits or severe pain which has not responded to conservative treatment. Conditions where spinal fusion may be considered include, but are not limited to, degenerative disc disease, spinal disc herniation, discogenic pain, spinal tumor, vertebral fracture, scoliosis, kyphosis (i.e., Scheuermann's disease), spondylolisthesis, or spondylosis.

In certain embodiments, different methods of lumbar spinal fusion may be used in conjunction with each other. In one method, one places the bone graft between the transverse processes in the back of the spine. These vertebrae are fixed in place with screws and/or wire through the pedicles of each vertebra attaching to a metal rod on each side of the vertebrae. In another method, one places the bone graft between the vertebra in the area usually occupied by the intervertebral disc. In preparation for the spinal fusion, the disc is removed entirely. A device may be placed between the vertebrae to maintain spine alignment and disc height. The intervertebral device may be made from either plastic or titanium or other suitable material. The fusion then occurs between the endplates of the vertebrae. Using both types of fusion are contemplated.

Therapeutic Applications

In some embodiments, the disclosure relates to pharmaceutical compositions comprising compounds disclosed herein for therapeutic applications. In some embodiments, the disclosure relates to methods of treating bone degenerative disorders, such as osteoporosis, osteitis deformans ("Paget's disease of bone"), bone metastasis (with or without hypercalcaemia), multiple myeloma, primary hyperparathyroidism, or osteogenesis imperfecta. Osteoporosis is a disease of bones that leads to an increased risk of fracture. In osteoporosis, the bone mineral density (BMD) is reduced, bone microarchitecture is disrupted, and the amount and variety of proteins in bone is altered. Osteoporosis is most common in women after menopause, when it is called postmenopausal osteoporosis, but may also develop in men, and may occur in anyone in the presence of particular hormonal disorders and other chronic diseases or as a result of medications, specifically glucocorticoids, when the disease is called steroid- or glucocorticoid-induced osteoporosis (SIOP or GIOP).

Osteoporotic fractures are those that occur in situations where healthy people would not normally break a bone; they are therefore regarded as fragility fractures. Typical fragility fractures occur in the vertebral column, rib, hip and wrist. The diagnosis of osteoporosis can be made using conventional radiography by measuring the bone mineral density (BMD).

In some embodiments, the disclosure relates to treating bone degenerative disorders by administering pharmaceutical composition described herein in combination with other agents, such as calcium carbonate and calcium citrate, vitamin D, cholecalciferol, 1,25-dihydroxycholecalciferol, calcitriol, estrogen, testosterone, raloxifene, pamidronate, neridronate, olpadronate, alendronate (Fosamax), ibandronate (Boniva), risedronate (Actonel), zoledronate (Zometa, Aclasta), etidronate (Didronel), clodronate (Bonefos, Loron), or tiludronate (Skelid).

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds of the disclosure contain a hydrogen-donating heteroatom (e.g. NH), the disclosure also covers salts and/or isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxy group is bonded to any group that, when administered to a mammalian subject, cleaves to form a free hydroxy group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds of formula I can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

EXPERIMENTAL

Compound Screenings

Compounds were selected by virtual screening for development based on computational modeling, docking, and in silico screening. It was desirable for the compounds to possess features similar to the PPXY motif of Smads (natural target proteins) that interact with Smurf1, as shown by Ludi3 docking scores. (See Sangadala et al. (2007) Proteins 68: 690-701 and FIG. 2). The BMP-potentiating activities of compounds may be evaluated by monitoring several markers of the osteoblastic phenotype corresponding to various time points during phenotype differentiation of C2C12 cells towards terminally differentiated osteoblasts.

Cell Culture

Mouse C2C12 cells and Dulbecco's modified Eagle's medium (DMEM) were purchased from ATCC (Manassas, Va.). The non-heat inactivated fetal bovine serum (FBS) was purchased from HyClone Laboratories, Inc. (Logan, Utah). The C2C12 cells at passages 5 to 10 were subcultured in T-75 cm$^2$ flasks in DMEM supplemented with 10% FBS at 37° C. in 5% $CO_2$ with humidification. When the flasks reached 80% confluence, the cells were trypsinized and seeded in triplicate at 200,000 cells/well in a 6-well plate for quantitative real-time RT-PCR and alkaline phosphatase (ALP) assays or at 50,000 cells/well in a 12-well plate for the dual-luciferase reporter assay.

RNA Extraction and Reverse Transcription

The C2C12 cells were plated at a density of 200,000 cells/well in 6-well plates and grown overnight in DMEM containing 10% FBS. On day 2, the culture medium was replaced with DMEM containing 2% FBS and the cells were treated with various concentrations of Smurf1-interacting compound (diluted from 10 mg/ml stock solutions prepared in DMSO) for 24 hours. In control cultures, a DMSO solvent concentration of 0.01% (v/v) was applied. On day 3, medium was replaced with fresh DMEM containing 2% FBS and the cells were treated with BMP-2 for 24 hours.

Total RNA was harvested using the RNeasy Mini Kit according to the manufacturer's instructions (Qiagen, Valencia, Calif.). The harvested RNA was digested with RNase-free DNase I (Qiagen, Valencia, Calif.) to remove DNA contamination. The concentration of the isolated RNA was determined by measuring the absorbance at 260 nm wave length with a spectrophotometer (Model DU 640, Beckman Coulter, Inc. Brea, Calif.). The ratio of A260/A280 was between 1.6 and 1.8. Reverse transcription was carried out to synthesize cDNA in a 100 µl volume with 2 µg of total RNA, 10×RT buffer, 5.5 mM MgCl2, 2 mM dNTP mixture, 0.125 µM oligo d(T), 0.125 µM random primer, 40 Units of RNase inhibitor, and 125 Units of MultiScribe (Applied Biosystems, Foster City, Calif.) for 10 minutes at 25° C., 30 minutes at 48° C., and 5 minutes at 95° C.

Quantitative Real-Time RT-PCR

Quantitative real-time RT-PCR was performed to determine the mRNA expression level of ALP and osteocalcin. The sequences of the primers were as follows: ALP (forward, 5'-TCA GGG CAA TGA GGT CAC ATC-3'; (SEQ ID NO: 6), reverse, 5'-CAC AAT GCC CAC GGA CTT C-3') (SEQ ID NO: 7, osteocalcin (forward, 5'-CGG CCC TGA GTC TGA CAA AG-3'; (SEQ ID NO: 8) reverse, 5'-CTC GTC ACA AGC AGG GTC AA-3' (SEQ ID NO: 9)). Twenty-five microliters of reaction volume included 5 µl of cDNA, 0.5 µl of 10 µM of each primer and 12.5 µl of 2×SYBR green master mix (Applied Biosystems). Real-time PCR was performed with the following three-step protocol: step 1, 50° C. for 2 minutes; step 2, 95° C. for 10 minutes; step 3, 40 cycles of 95° C. for 15 seconds and 62° C. for 1 minute using the 7500 real-time PCR System (Applied Biosystems, Foster City, Calif.). To confirm the amplification specificity, the PCR products were subjected to a dissociation curve analysis. The threshold cycles (Ct) of each reaction were normalized to those obtained for 18S mRNA using the −ΔΔCt method (Applied Biosystems). All PCR reactions were performed in triplicate.

Alkaline Phosphatase (ALP) Assay

The C2C12 cells were plated at 200,000 cells/well in 6-well plates and grown overnight in DMEM containing 10% FBS. On day 2, the culture medium was replaced with DMEM containing 2% FBS and the cells were treated with various concentrations of the Smurf1-interacting compound for 24 hours. On day 3, the medium was replaced with fresh DMEM containing 2% FBS and the cells were treated with 50 ng/ml of BMP-2 with or without compound for 72 hours. The cells were washed with phosphate-buffered saline (PBS) and lysed by addition of lysis buffer (10 mM Tris-HCl pH 8.0, 1 mM MgCl2 and 0.5% Triton X-100). The cell lysates were centrifuged for 5 minutes at 13,000×g. The supernatant was removed and the aliquots were assayed for ALP activity and protein amount. The ALP activity was measured in triplicate using an ALP assay kit (Sigma-Aldrich, St. Louis, Mo.) in microtiter plates. The protein amount was determined with Bio-Rad protein assay reagent (Bio-Rad, Hercules, Calif.) using bovine serum albumin (BSA) as a standard. The ALP activity (nmoles of p-nitrophenol per ml) was normalized to the protein amount (nmoles of p-nitrophenol per µg).

Dual-Luciferase Reporter Assay

A BMP-specific Smad1-driven 9×GCCG (a consensus binding sequence for Smad1) reporter plasmid was used. The C2C12 cells were trypsinized and seeded in triplicate wells at 50,000 cells/well in 12-well plates on day 1. On day 2, the cells were cotransfected with the 9×GCCG-reporter construct and the renilla-luciferase control vector using SuperFect (Qiagen, Valencia, Calif.) for 24 hrs. A total of 1 µg of plasmids was used for cotransfection in each well, and the concentration of renilla-luciferase vector was 1/15 of the 9×GCCG-reporter plasmid. On day 3, medium was replaced with DMEM containing 2% FBS and the cells were treated with various concentrations of the Smurf1-interacting compound. On day 4, the cells were treated with BMP-2. On day 5, the luciferase activities were measured in 20 µl of cell-lysate using the dual-luciferase assay system (Promega, Madison, Wis.) with a luminometer (LumiCount; Packard Bioscience, Meriden, Conn.) following the manufacturer's instructions. The luciferase activity was expressed as relative units of luciferase (RUL; a ratio of firefly luciferase to renilla luciferase activity).

Determination of $EC_{50}$

The $EC_{50}$ values were calculated by determining the concentration by which 50% of maximum activity was reached using the sigmoidal fit equation. The 50% effective concentrations were determined with the standard curve analysis of SigmaPlot 8.02. The nonlinear regression equation is $y = min + (max - min)/(1 + (x/EC_{50})Hill\ Slope)$ where y is the observed responses; x is the dose concentration; max and min are approximated by the program automatically during the calculation. Values were not extrapolated beyond the tested range of concentrations.

The invention claimed is:

1. A bone graft composition comprising a 2,4-diamino-1,3,5-triazine derivative or salt thereof and further comprising collagen, wherein the 2,4-diamino-1,3,5-triazine derivative is a compound of the following formula:

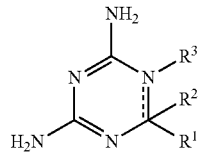

or salts thereof, wherein
if ---- is a single bond then
$R^3$ is alkyl, phenyl, benzyl, carbocyclyl, aryl, or heterocyclyl wherein $R^3$ is optionally substituted with one or more the same or different $R^4$;
$R^2$ is hydrogen or alkyl; and
$R^1$ is hydrogen or alkyl; or
if ---- is a double bond then
$R^2$ and $R^3$ are absent;
$R^1$ is alkyl, alkenyl, carbocyclyl, aryl, or heterocyclyl wherein $R^3$ is optionally substituted with one or more the same or different $R^4$, $R^4$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and
$R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

2. The bone graft composition of claim 1, wherein the 2,4-diamino-1,3,5-triazine derivative is a compound selected from the group consisting of:
1-benzyl-4,6-diamino-1,2-dihydro-2,2-dimethyl-1,3,5-triazine;
1-(4-methoxybenzyl)-4,6-diamino-1,2-dihydro-2,2-dimethyl-1,3,5-triazine;
1-(3-methoxybenzyl)-4,6-diamino-1,2-dihydro-2,2-dimethyl-1,3,5-triazine;
1-(4-chlorophenyl)-4,6-diamino-1,2-dihydro-2,2-dimethyl-1,3,5-triazine;
1-(3-chlorophenyl)-4,6-diamino-1,2-dihydro-2,2-dimethyl-1,3,5-triazine;
1-(3-chloro-4-methoxyphenyl)-4,6-diamino-1,2-dihydro-2,2-dimethyl-1,3,5-triazine;
1-(3-chloro-4-methylphenyl)-4,6-diamino-1,2-dihydro-2,2-dimethyl-1,3,5-triazine;
1-(4-bromo-2-fluorophenyl)-4,6-diamino-1,2-dihydro-2,2-dimethyl-1,3,5-triazine;
1-(2-bromo-4-methylphenyl)-4,6-diamino-1,2-dihydro-2,2-dimethyl-1,3,5-triazine;
6,6-dimethyl-1-(4-methyl-3-nitrophenyl)-1,6-dihydro-1,3,5-triazine-2,4-diamine;
1-(3-chloro-4-fluorophenyl)-4,6-diamino-1,2-dihydro-2,2-dimethyl-1,3,5-triazine;
1-(3-chloro-5-fluorophenyl)-4,6-diamino-1,2-dihydro-2,2-dimethyl-1,3,5-triazine;
2-chloro-4-(4,6-diamino-2,2-dimethyl-1,3,5-triazin-1(2H)-yl)phenol;
1-(2-chloro-5-methoxyphenyl)-4,6-diamino-1,2-dihydro-2,2-dimethyl-1,3,5-triazine; and
1-(2-chloro-4-methylphenyl)-4,6-diamino-1,2-dihydro-2,2-dimethyl-1,3,5-triazine or salts thereof.

3. The bone graft composition of claim 1, further comprising a growth factor.

4. The bone graft composition of claim 3, wherein the growth factor is a bone morphogenetic protein.

5. The bone graft composition of claim 4, wherein the bone morphogenetic protein is BMP-2, BMP-7, BMP-6, or BMP-9.

6. A bone graft composition comprising a 2,4-diamino-1,3,5-triazine derivative or salt thereof and further comprising calcium phosphates, wherein the 2,4-diamino-1,3,5-triazine derivative is a compound of the following formula:

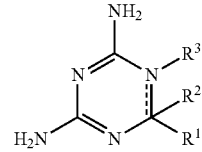

or salts thereof, wherein
if ---- is a single bond then
$R^3$ is alkyl, phenyl, benzyl, carbocyclyl, aryl, or heterocyclyl wherein $R^3$ is optionally substituted with one or more the same or different $R^4$;

R² is hydrogen or alkyl; and
R¹ is hydrogen or alkyl; or
if ---- is a double bond then
R² and R³ are absent;
R¹ is alkyl, alkenyl, carbocyclyl, aryl, or heterocyclyl wherein R³ is optionally substituted with one or more the same or different R⁴, R⁴ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkyl sulfonyl, aryl sulfonyl, carbocyclyl, aryl, or heterocyclyl, wherein R⁴ is optionally substituted with one or more, the same or different, R⁵; and
R⁵ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

7. The bone graft composition of claim 6, wherein the 2,4-diamino-1,3,5-triazine derivative is a compound selected from the group consisting of:
1-benzyl-4,6-diamino-1,2-dihydro-2,2-dimethyl-1,3,5-triazine;
1-(4-methoxybenzyl)-4,6-diamino-1,2-dihydro-2,2-dimethyl-1,3,5-triazine;
1-(3-methoxybenzyl)-4,6-diamino-1,2-dihydro-2,2-dimethyl-1,3,5-triazine;
1-(4-chlorophenyl)-4,6-diamino-1,2-dihydro-2,2-dimethyl-1,3,5-triazine;
1-(3-chlorophenyl)-4,6-diamino-1,2-dihydro-2,2-dimethyl-1,3,5-triazine;
1-(3-chloro-4-methoxyphenyl)-4,6-diamino-1,2-dihydro-2,2-dimethyl-1,3,5-triazine;
1-(3-chloro-4-methylphenyl)-4,6-diamino-1,2-dihydro-2,2-dimethyl-1,3,5-triazine;
1-(4-bromo-2-fluorophenyl)-4,6-diamino-1,2-dihydro-2,2-dimethyl-1,3,5-triazine;
1-(2-bromo-4-methylphenyl)-4,6-diamino-1,2-dihydro-2,2-dimethyl-1,3,5-triazine;
6,6-dimethyl-1-(4-methyl-3-nitrophenyl)-1,6-dihydro-1,3,5-triazine-2,4-diamine;
1-(3-chloro-4-fluorophenyl)-4,6-diamino-1,2-dihydro-2,2-dimethyl-1,3,5-triazine;
1-(3-chloro-5-fluorophenyl)-4,6-diamino-1,2-dihydro-2,2-dimethyl-1,3,5-triazine;
2-chloro-4-(4,6-diamino-2,2-dimethyl-1,3,5-triazin-1(2H)-yl)phenol;
1-(2-chloro-5-methoxyphenyl)-4,6-diamino-1,2-dihydro-2,2-dimethyl-1,3,5-triazine; and
1-(2-chloro-4-methylphenyl)-4,6-diamino-1,2-dihydro-2,2-dimethyl-1,3,5-triazine or salts thereof.

8. The bone graft composition of claim 6, wherein said calcium phosphates are hydroxyapatite and tricalcium phosphate.

9. The bone graft composition of claim 6, wherein said calcium phosphates are in physiologically compatible bone granules.

10. The bone graft composition of claim 6, further comprising a growth factor.

11. The bone graft composition of claim 10, wherein the growth factor is a bone morphogenetic protein.

12. The bone graft composition of claim 11, wherein the bone morphogenetic protein is BMP-2, BMP-7, BMP-6, or BMP-9.

13. The bone graft composition of claim 6, further comprising hydrogel polymer.

14. A bone graft composition comprising a 2,4-diamino-1,3,5-triazine derivative or salt thereof and further comprising bioglass, wherein the 2,4-diamino-1,3,5-triazine derivative is a compound of the following formula:

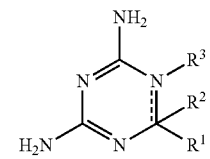

or salts thereof, wherein
if ---- is a single bond then
R³ is alkyl, phenyl, benzyl, carbocyclyl, aryl, or heterocyclyl wherein R³ is optionally substituted with one or more the same or different R⁴;
R² is hydrogen or alkyl; and
R¹ is hydrogen or alkyl; or
if ---- is a double bond then
R² and R³ are absent;
R¹ is alkyl, alkenyl, carbocyclyl, aryl, or heterocyclyl wherein R³ is optionally substituted with one or more the same or different R⁴, R⁴ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkyl sulfonyl, aryl sulfonyl, carbocyclyl, aryl, or heterocyclyl, wherein R⁴ is optionally substituted with one or more, the same or different, R⁵; and
R⁵ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

15. The bone graft composition of claim 14, wherein the 2,4-diamino-1,3,5-triazine derivative is a compound selected from the group consisting of:
1-benzyl-4,6-diamino-1,2-dihydro-2,2-dimethyl-1,3,5-triazine;
1-(4-methoxybenzyl)-4,6-diamino-1,2-dihydro-2,2-dimethyl-1,3,5-triazine;
1-(3-methoxybenzyl)-4,6-diamino-1,2-dihydro-2,2-dimethyl-1,3,5-triazine;
1-(4-chlorophenyl)-4,6-diamino-1,2-dihydro-2,2-dimethyl-1,3,5-triazine;

1-(3-chlorophenyl)-4,6-diamino-1,2-dihydro-2,2-dimethyl-1,3,5-triazine;
1-(3-chloro-4-methoxyphenyl)-4,6-diamino-1,2-dihydro-2,2-dimethyl-1,3,5-triazine;
1-(3-chloro-4-methylphenyl)-4,6-diamino-1,2-dihydro-2,2-dimethyl-1,3,5-triazine;
1-(4-bromo-2-fluorophenyl)-4,6-diamino-1,2-dihydro-2,2-dimethyl-1,3,5-triazine;
1-(2-bromo-4-methylphenyl)-4,6-diamino-1,2-dihydro-2,2-dimethyl-1,3,5-triazine;
6,6-dimethyl-1-(4-methyl-3-nitrophenyl)-1,6-dihydro-1,3,5-triazine-2,4-diamine;
1-(3-chloro-4-fluorophenyl)-4,6-diamino-1,2-dihydro-2,2-dimethyl-1,3,5-triazine;
1-(3-chloro-5-fluorophenyl)-4,6-diamino-1,2-dihydro-2,2-dimethyl-1,3,5-triazine;
2-chloro-4-(4,6-diamino-2,2-dimethyl-1,3,5-triazin-1(2H)-yl)phenol;
1-(2-chloro-5-methoxyphenyl)-4,6-diamino-1,2-dihydro-2,2-dimethyl-1,3,5-triazine; and
1-(2-chloro-4-methylphenyl)-4,6-diamino-1,2-dihydro-2,2-dimethyl-1,3,5-triazine or salts thereof.

16. The bone graft composition of claim 6, further comprising a growth factor.

17. The bone graft composition of claim 10, wherein the growth factor is a bone morphogenetic protein.

18. The bone graft composition of claim 11, wherein the bone morphogenetic protein is BMP-2, BMP-7, BMP-6, or BMP-9.

\* \* \* \* \*